(12) United States Patent
Ueda et al.

(10) Patent No.: US 11,792,949 B2
(45) Date of Patent: *Oct. 17, 2023

(54) DEVICE INCLUDING A CIRCUIT MEMBER SEALED BY A FILM, AND METHOD OF FORMING THE DEVICE

(71) Applicant: JAPAN AVIATION ELECTRONICS INDUSTRY, LIMITED, Tokyo (JP)

(72) Inventors: Shinji Ueda, Tokyo (JP); Osamu Hashiguchi, Tokyo (JP)

(73) Assignee: JAPAN AVIATION ELECTRONICS INDUSTRY, LIMITED, Tokyo (JP)

( * ) Notice: Subject to any disclaimer, the term of this patent is extended or adjusted under 35 U.S.C. 154(b) by 81 days.

This patent is subject to a terminal disclaimer.

(21) Appl. No.: 17/499,002

(22) Filed: Oct. 12, 2021

(65) Prior Publication Data

US 2022/0192043 A1 Jun. 16, 2022

(30) Foreign Application Priority Data

Dec. 11, 2020 (JP) .................................. 2020-205499

(51) Int. Cl.
*H05K 5/06* (2006.01)
*H05K 1/11* (2006.01)

(52) U.S. Cl.
CPC .............. *H05K 5/069* (2013.01); *H05K 1/11* (2013.01)

(58) Field of Classification Search
CPC ...... H05K 9/0043; H05K 5/069; H05K 5/068; H05K 5/066; H05K 1/11; A61B 5/02444; A61B 5/02438; A61B 5/024
See application file for complete search history.

(56) References Cited

U.S. PATENT DOCUMENTS 3,910,008 A 10/1975 Johnson
4,933,042 A * 6/1990 Eichelberger ........... H01L 21/56
156/289

(Continued)

FOREIGN PATENT DOCUMENTS

CN 201545294 U 8/2010
JP 2001233383 A 8/2001

(Continued)

OTHER PUBLICATIONS

Extended European Search Report (EESR) dated Apr. 25, 2022, issued in counterpart European Application No. 21204222.0.

(Continued)

*Primary Examiner* — James Wu
(74) *Attorney, Agent, or Firm* — Holtz, Holtz & Volek PC

(57) ABSTRACT

A device includes a first sealing member including a first film, a second sealing member, a first circuit member including a first contact point, and a second circuit member including a second contact point. The device defines a closed space which is enclosed by the first sealing member and the second sealing member and is shut off from an outer space outside the device. The first circuit member and the second circuit member are shut in the closed space. At least one of the first sealing member and the second sealing member includes an uneven portion. The uneven portion is in contact with at least one of the first circuit member and the second circuit member and covers a predetermined region which corresponds to at least one of the first contact point and the second contact point.

20 Claims, 12 Drawing Sheets

(56) References Cited

U.S. PATENT DOCUMENTS

| | | | | |
|---|---|---|---|---|
| 5,285,619 A | * | 2/1994 | Jones | H05K 9/0043 |
| | | | | 53/472 |
| 5,605,547 A | | 2/1997 | Lake | |
| 7,498,099 B2 | | 3/2009 | Otohata et al. | |
| 2015/0155530 A1 | * | 6/2015 | Takahashi | H01M 50/129 |
| | | | | 429/127 |
| 2022/0319938 A1 | * | 10/2022 | Ueda | H05K 9/0043 |
| | | | | 53/472 |
| 2022/0322518 A1 | * | 10/2022 | Ueda | H05K 1/0272 |

FOREIGN PATENT DOCUMENTS

| | | | |
|---|---|---|---|
| JP | 2001332654 A | 11/2001 | |
| JP | 2003258413 A | 9/2003 | |

OTHER PUBLICATIONS

Korean Office Action (and an English language translation thereof) dated Mar. 20, 2023, issued in counterpart Korean Application No. 10-2021-0140090.

* cited by examiner

DEVICE INCLUDING A CIRCUIT MEMBER SEALED BY A FILM, AND METHOD OF FORMING THE DEVICE

CROSS REFERENCE TO RELATED APPLICATIONS

This application is based on and claims priority under 35 U.S.C. § 119 to Japanese Patent Application No. JP 2020-205499 filed Dec. 11, 2020, the content of which is incorporated herein in its entirety by reference.

BACKGROUND OF THE INVENTION

This invention relates to a device comprising a circuit member sealed by a film.

For example, a device which can be made thinner is disclosed in JP2001-332654A (Patent Document 1), the content of which is incorporated herein by reference.

Referring to FIG. 23, Patent Document 1 discloses a module (device) 90 with built-in semiconductor chips. The device 90 comprises a thermosetting resin composition (sealing resin) 92 and a circuit member 94 including semiconductor chips 96 and wiring patterns 98. The sealing resin 92 is formed so that the circuit member 94 is embedded therewithin. Then, a surface of the sealing resin 92 is polished so that the device 90 is made thinner.

Further reduction in thickness is required for a device comprising a circuit member.

SUMMARY OF THE INVENTION

It is therefore an object of the present invention to provide a new device which can be made thinner.

An aspect of the present invention provides a device comprising a first sealing member, a second sealing member, a first circuit member and a second circuit member. The first sealing member basically comprises a first film formed of a film. The device is formed with a closed space. The closed space is enclosed by the first sealing member and the second sealing member and is shut off from an outer space outside the device. The first circuit member and the second circuit member are shut in the closed space. The first circuit member comprises a first contact point. The second circuit member comprises a second contact point. The first contact point and the second contact point are in contact with each other. At least one of the first sealing member and the second sealing member is provided with an uneven portion. The uneven portion is in contact with at least one of the first circuit member and the second circuit member and covers a predetermined region which corresponds to at least one of the first contact point and the second contact point.

Another aspect of the present invention provides a forming method of a device comprising a first sealing member, a second sealing member, a first circuit member and a second circuit member. The forming method comprises a preparing step, a stacking step, shutting-in step and a vacuuming step. In the preparing step, the first sealing member, the second sealing member, the first circuit member and the second circuit member are prepared. The first sealing member basically comprises a first film formed of a film. The first film is provided with an air valve. At least one of the first sealing member and the second sealing member is provided with an uneven portion. The first circuit member comprises a first contact point. The second circuit member comprises a second contact point. In the stacking step, the first sealing member, the first circuit member, the second circuit member and the second sealing member are stacked on each other in this order. The first contact point and the second contact point face each other. The uneven portion faces at least one of the first circuit member and the second circuit member. The uneven portion covers a predetermined region which corresponds to at least one of the first contact point and the second contact point. In the shutting-in step, the first circuit member and the second circuit member are shut in an inner space which is formed in the device. The inner space is enclosed by the first sealing member and the second sealing member and is shut off from an outer space outside the device except for the air valve. In the vacuuming step, the inner space is vacuumed by using the air valve so that the first contact point and the second contact point are brought into contact with each other.

According to the device of an aspect of the present invention, the first sealing member and the second sealing member overlap with each other while the first circuit member and the second circuit member (hereafter, simply referred to as "circuit members") are sandwiched therebetween. The first sealing member is basically formed of a film. Moreover, the structure of each of the circuit members is not restricted except that each of the circuit members should be provided with the contact point. Thus, each of the circuit members of an aspect of the present invention has a simple structure and can be formed of various material. For example, each of the circuit members may be an insulation film formed with a conductive pattern having the contact point. In this instance, the thickness of the entire device can be made extremely thin. Thus, an aspect of the present invention provides a new device which can be made thinner.

An appreciation of the objectives of the present invention and a more complete understanding of its structure may be had by studying the following description of the preferred embodiment and by referring to the accompanying drawings.

Figure 1:
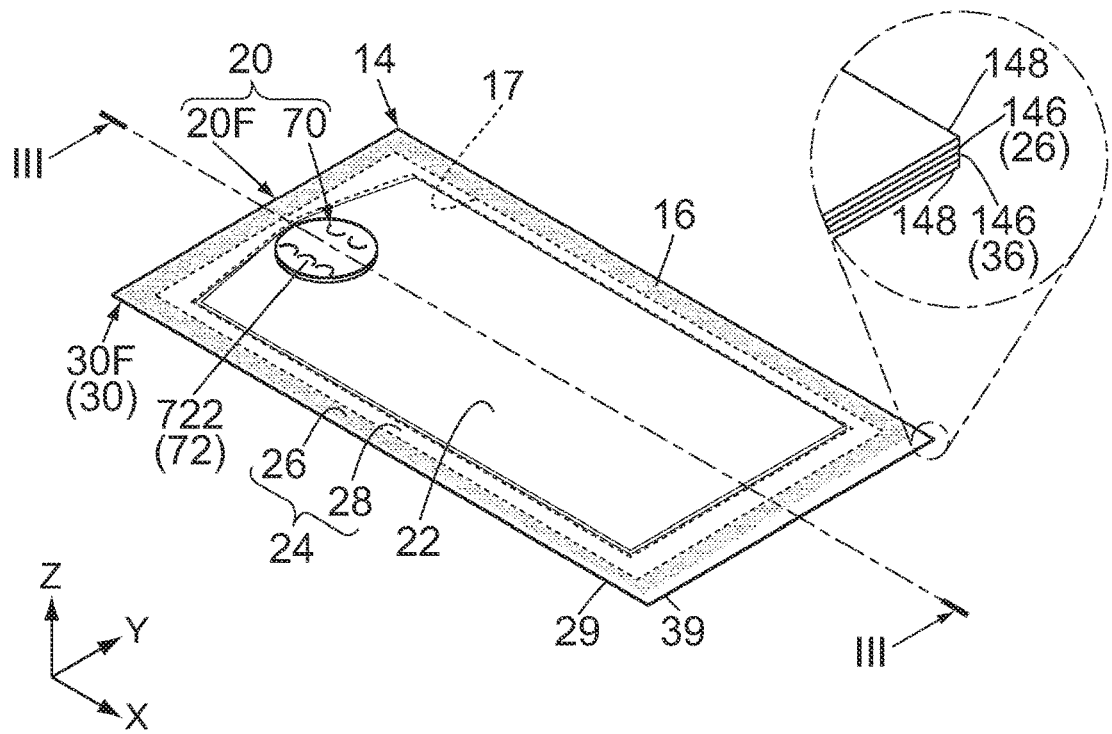
FIG. 1 is a perspective view showing a device according to an embodiment of the present invention, wherein boundary lines of a contact region formed between a first sealing member and a second sealing member are illustrated with dashed line, and a part of the device enclosed by chain dotted lines is enlarged and illustrated.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DESCRIPTION OF PREFERRED EMBODIMENTS

Referring to FIG. 1, a device 10 according to an embodiment of the present invention is an independent electronic device. More specifically, the device 10 can work solely without physically attached to another electronic device (not shown). For example, the device 10 measures the heart rate of a subject by attaching the device 10 near the heart of the subject and transmits the measurement result to another electronic device. Thus, the device 10 can be used as an electronic device for measuring biological information such as heart rate. However, the present invention is not limited thereto but is applicable to various devices having various functions.

Figure 2:
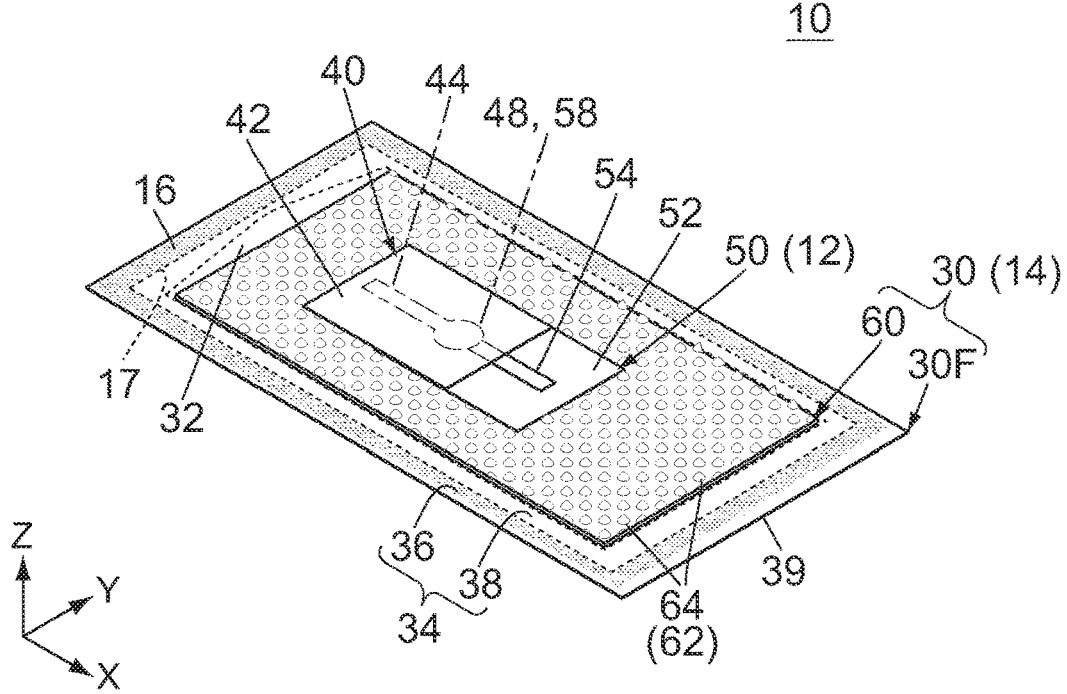
FIG. 2 is a perspective view showing the device of FIG. 1, wherein the first sealing member is removed, and boundary lines of the contact region are illustrated with dashed line.

Referring to FIG. 2 together with FIG. 1, the device 10 of the present embodiment comprises a circuit structure 12 and a sealing member 14. The circuit structure 12 is a member for enabling the device 10 to work as an electronic device. For example, the circuit structure 12 has an electronic circuit (not shown) for measuring heart rate and another electronic circuit (not shown) for transmitting the measurement result to another electronic device (not shown). The sealing member 14 entirely accommodates the circuit structure 12 therewithin and protects the circuit structure 12 from an external environment. Thus, the circuit structure 12 is shut in the sealing member 14.

The circuit structure 12 of the present embodiment comprises a first circuit member 40 and a second circuit member 50. The sealing member 14 of the present embodiment comprises a first sealing member 20 and a second sealing member 30. Thus, the device 10 comprises the first sealing member 20, the second sealing member 30, the first circuit member 40 and the second circuit member 50.

Figure 7:
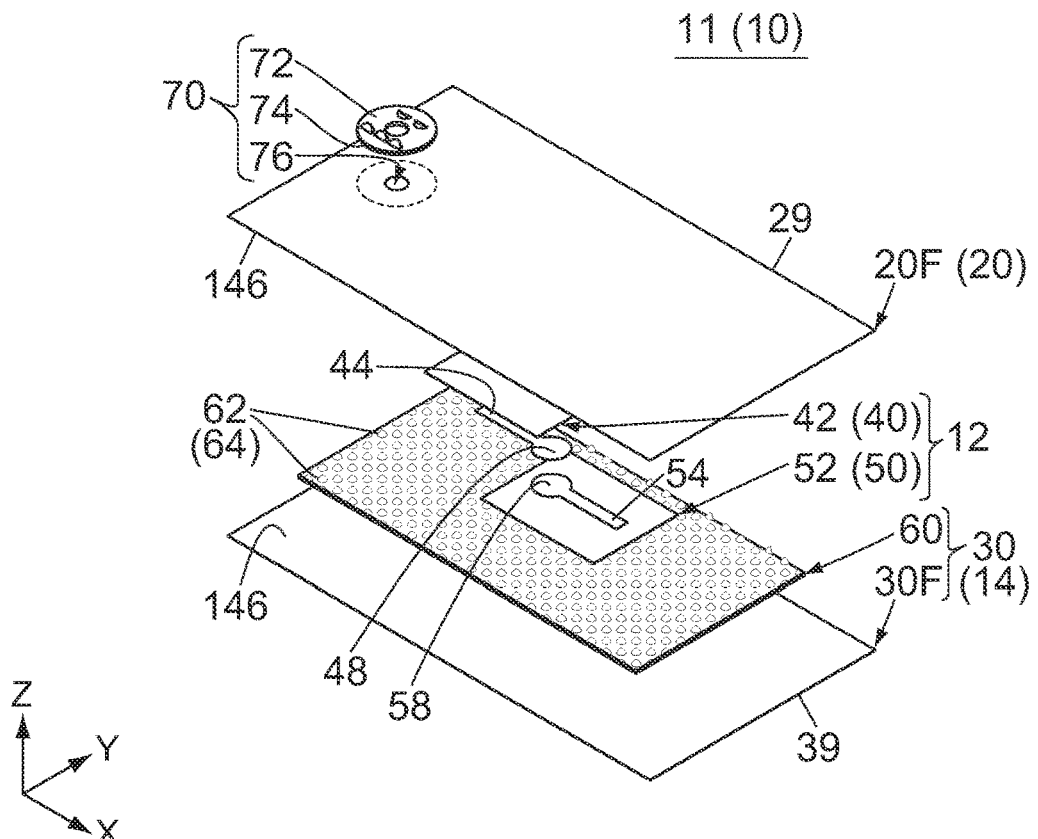
FIG. 7 is a perspective view showing a device material set which is prepared in a preparing step of the forming method of FIG. 6, wherein a part of a first film which corresponds to an air valve is illustrated with dashed line.

Referring to FIG. 7 together with FIGS. 1 and 2, the aforementioned four members, i.e., the first sealing member 20, the second sealing member 30, the first circuit member 40 and the second circuit member 50 of the device 10, are stacked in an upper-lower direction (Z-direction) and are combined to form the device 10 as a single structure. The device 10 of the present embodiment comprises only the aforementioned four members. However, the present invention is not limited thereto, but the device 10 may further comprise another member in addition to the aforementioned four members.

Hereafter, explanation will be made about each member of the device 10 of the present embodiment.

Referring to FIG. 7, the first sealing member 20 of the present embodiment is formed of a first film 20F as its base material. The first film 20F is an insulation film. In other words, the first sealing member 20 basically comprises the first film 20F formed of a film. The first film 20F of the present embodiment is a thin, rectangular sheet and is bendable. The first film 20F extends in parallel to a horizontal plane (sheet plane: XY-plane). The first film 20F has a peripheral edge 29 in the XY-plane. The first film 20F is formed of a hole 76. The hole 76 passes through the first film 20F in the upper-lower direction (Z-direction) perpendicular to the XY-plane.

Figure 8:
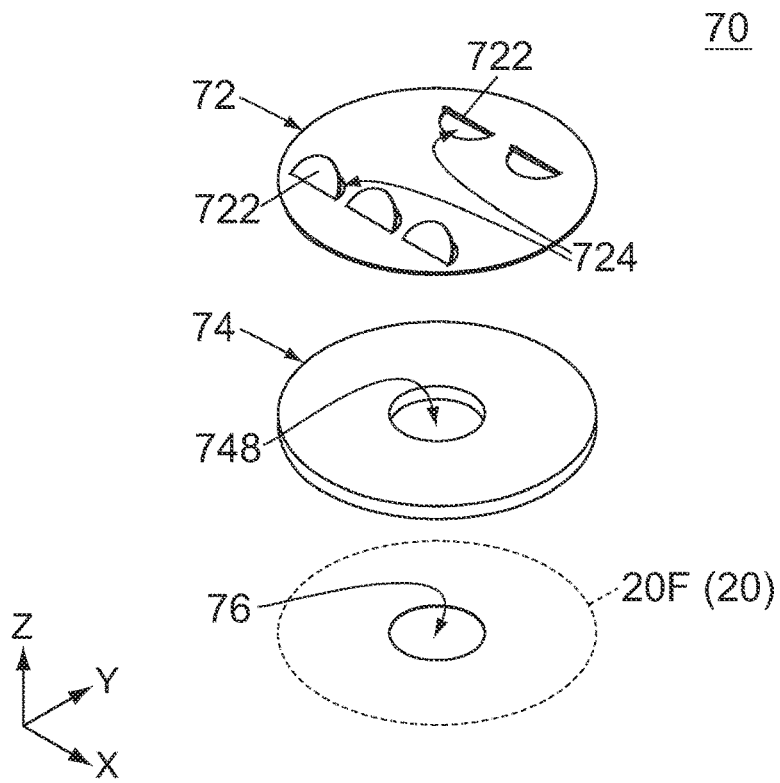
FIG. 8 is a perspective view showing the air valve of FIG. 7.

Referring to FIGS. 1 and 7, the first sealing member 20 of the present embodiment comprises an air valve 70 in addition to the first film 20F. Referring to FIGS. 7 and 8, the air valve 70 comprises a cover portion 72 formed of a thin insulation film and a base portion 74 made of insulator. As shown in FIG. 8, the base portion 74 is formed with a passing hole 748. The passing hole 748 passes through the base portion 74 in the Z-direction. The cover portion 72 is formed with five valves 722 and five cuts 724 which correspond to the valves 722, respectively. Each of the cuts 724 passes through the cover portion 72 in the Z-direction. The valves 722 and the cuts 724 are located inward of an outer circumference of the cover portion 72 in the XY-plane.

Referring to FIG. 8 together with FIG. 7, the cover portion 72 is adhered to and fixed on an upper surface (positive Z-side surface) of the base portion 74. In particular, the outer circumference of the cover portion 72 in the XY-plane is tightly adhered to the upper surface of the base portion 74 throughout entire circumference. In contrast, an inner part of the cover portion 72, which is located inward of the outer circumference of the cover portion 72 in the XY-plane, can be pulled away from the upper surface of the base portion 74. Thus, a passage which allows air to pass therethrough can be formed between the passing hole 748 and each of the cuts 724. The base portion 74 has a lower surface (negative Z-side surface) which is adhered to and fixed on the first film 20F in such a way that the passing hole 748 communicate with the hole 76 of the first film 20F. Thus, the first film 20F is provided with the air valve 70.

Referring to FIG. 1 together with FIG. 8, the air valve 70 can take either an open state shown in FIG. 8 or a closed state shown in FIG. 1. When the air valve 70 takes the open state, each of the valves 722 is apart from the corresponding cut 724. When the air valve 70 takes the closed state, each of the valves 722 completely covers the corresponding cut 724. When the air valve 70 takes the open state, an air passage is formed between the inside and the outside of the device 10 via the air valve 70. When the air valve 70 takes the closed state, the inside of the device 10 is shut off from the outside of the device 10.

As described later, the air valve 70 is used for vacuuming the inside of the device 10 upon fabrication of the device 10. The air valve 70 of the present embodiment has a structure suitable for this use. However, the present invention is not limited thereto. For example, the structure of the air valve 70 is not specifically limited, provided that the inside air of the device 10 can be discharged by using the air valve 70. Moreover, the inside of the device 10 may be vacuumed without provision of the air valve 70. In other words, the first sealing member 20 may comprise the air valve 70 as necessary. Thus, the first sealing member 20 may comprise only the first film 20F.

Referring to FIG. 7, the second sealing member 30 of the present embodiment is formed of a second film 30F as its base material. The second film 30F is an insulation film. In other words, the second sealing member 30 basically comprises the second film 30F formed of a film. The second film 30F of the present embodiment is a thin, rectangular sheet and is bendable. The second film 30F extends in parallel to the XY-plane. The second film 30F has a peripheral edge 39 in the XY-plane. However, the present invention is not limited thereto. For example, the second sealing member 30 may basically comprise a rigid circuit board, which has rigidity and is hard to be bent, instead of the second film 30F.

Referring to FIGS. 2 and 7, the second sealing member 30 of the present embodiment comprises an additional film 60 formed of an insulation film in addition to the second film 30F. The additional film 60 has an uneven portion 62. As described later, the uneven portion 62 is provided in order to maintain a passage which allows air to pass therethrough upon vacuuming the inside of the device 10. In detail, the uneven portion 62 is formed with a large number of projections 64. Each of the projections 64 is a projection which projects upward, or in the positive Z-direction, and is resiliently deformable. The projections 64 are uniformly and continuously formed over the entire additional film 60 in the XY-plane. According to the structure described above, a passage which allows air to pass therethrough is formed between every adjacent two of the projections 64. Each of the projections 64 may have any shape and any size, provided that the passage which allows air to pass therethrough can be formed.

Referring to FIG. 1 together with FIG. 2, the first film 20F and the second film 30F of the present embodiment overlap with each other so that the position of the peripheral edge 29 and the position of the peripheral edge 39 are aligned with each other in the XY-plane. However, the present invention is not limited thereto. For example, the size of the first film 20F in the XY-plane and the size of the second film 30F in the XY-plane may be different from each other. The shape of each of the first film 20F and the second film 30F is not limited to be rectangular but can be modified as necessary.

As shown in FIGS. 2 and 7, the first circuit member 40 of the present embodiment has a first base portion 42 and a first conductive pattern 44. The first base portion 42 of the present embodiment is a thin, rectangular sheet formed of an insulation film and is bendable. The first base portion 42 extends in parallel to the XY-plane. The first conductive pattern 44 is formed on the first base portion 42. In detail, the first conductive pattern 44 is made of conductor such as copper and is formed on a lower surface of the first base portion 42 by a forming method such as silver ink printing or etching.

The second circuit member 50 of the present embodiment has a second base portion 52 and a second conductive pattern 54. The second base portion 52 of the present embodiment is a thin, rectangular sheet formed of an insulation film and is bendable. The second base portion 52 extends in parallel to the XY-plane. The second conductive pattern 54 is formed on the second base portion 52. In detail, the second conductive pattern 54 is made of conductor such as copper and is formed on an upper surface of the second base portion 52 by a forming method such as silver ink printing or etching.

Each of the first circuit member 40 and the second circuit member 50 of the present embodiment has the aforementioned structure. However, the present invention is not limited thereto. For example, each of the first circuit member 40 and the second circuit member 50 may be provided with one or more electronic components. One of the first circuit member 40 and the second circuit member 50 may be a single electronic component. Each of the first circuit member 40 and the second circuit member 50 may be a rigid circuit board. The forming method of each of the first conductive pattern 44 and the second conductive pattern 54 is not specifically limited, provided that each of the first conductive pattern 44 and the second conductive pattern 54 is made of conductor.

Figure 3:
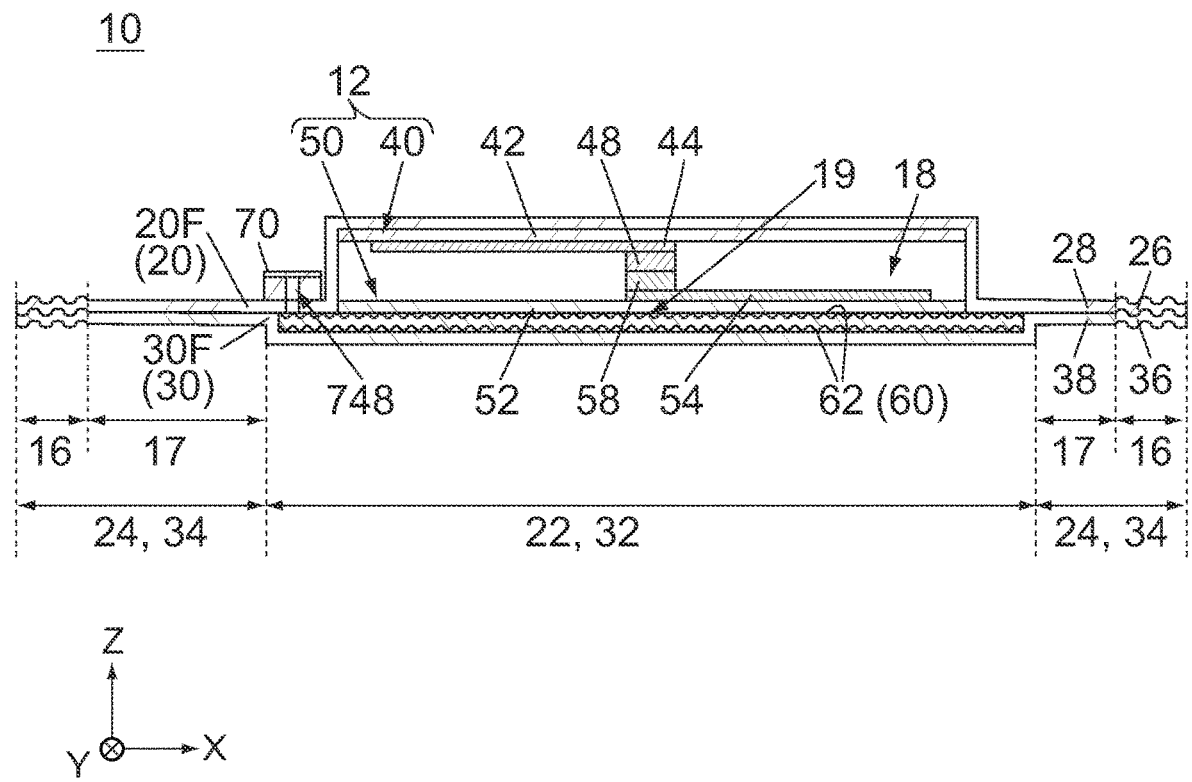
FIG. 3 is a schematic, cross-sectional view showing the device of FIG. 1, taken along line III-Ill, wherein an inner structure of the device is merely schematically illustrated, and the size and arrangement of each member are not equal to the actual size and arrangement thereof.

In the present embodiment, the first conductive pattern 44 has a first contact point 48, and the second conductive pattern 54 has a second contact point 58. Thus, the first circuit member 40 comprises the first contact point 48, and the second circuit member 50 comprises the second contact point 58. Referring to FIGS. 2 and 3, the first contact point 48 and the second contact point 58 are in contact with each other in the fabricated device 10. Thus, the first circuit member 40 and the second circuit member 50 are combined to each other so that the first contact point 48 and the second contact point 58 are brought into contact with each other. As a result, the first conductive pattern 44 and the second conductive pattern 54 are electrically connected with each other.

The first conductive pattern 44 and the second conductive pattern 54 illustrated in FIGS. 2 and 3 are abstract conductive patterns for simple explanation about the present invention and have no specific function. In other words, even when the illustrated first contact point 48 and the illustrated second contact point 58 are brought into contact with each other, the device 10 does not work as an electronic device. The actual first conductive pattern 44 and the actual second conductive pattern 54 have the structure illustrated in FIGS. 4 and 5, for example.

Figure 4:
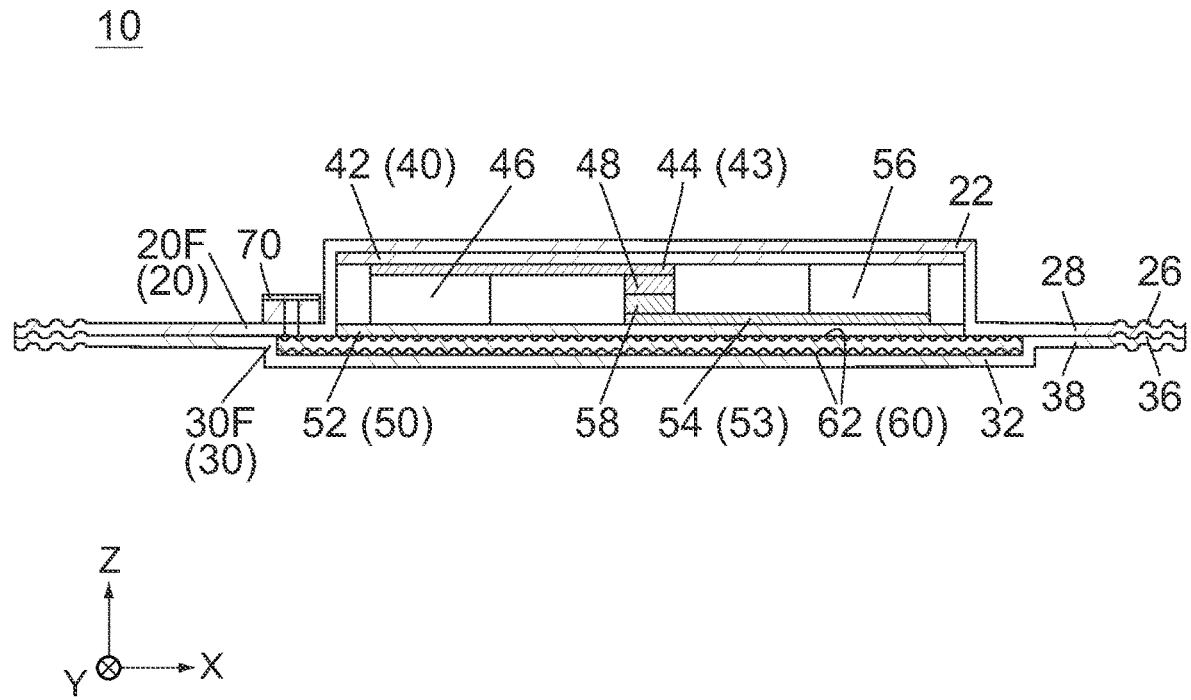
FIG. 4 is a cross-sectional view showing an example of the device of FIG. 3, wherein examples of a first conductive pattern of a first circuit member and a second conductive pattern of a second circuit member are illustrated, the inner structure of the device is merely schematically illustrated, and the size and arrangement of each member are not equal to the actual size and arrangement thereof.
Figure 5:
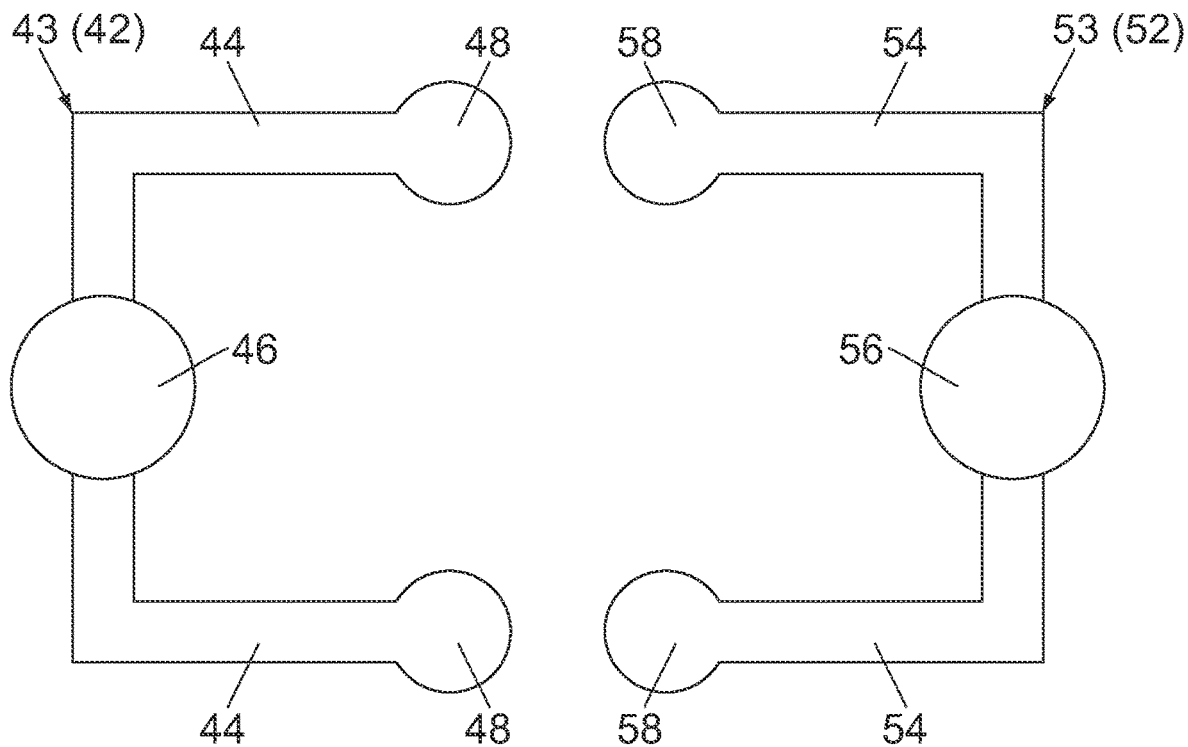
FIG. 5 is a view showing a circuit structure of the first conductive pattern and the second conductive pattern of FIG. 4, wherein although a first contact point of the illustrated first circuit is apart from a second contact point of the illustrated second circuit, the first contact point is actually located on the second contact point.

Referring to FIGS. 4 and 5, the first base portion 42 has a first circuit 43 formed on a lower surface thereof, and the second base portion 52 has a second circuit 53 formed on an upper surface thereof. The first circuit 43 has a coin battery 46 and two of the first conductive patterns 44 which are formed with the first contact points 48, respectively. The second circuit 53 has a light emitting diode (LED) 56 and two of the second conductive patterns 54 which are formed with the second contact points 58, respectively. When the first contact points 48 are brought into contact with the second contact points 58, respectively, the coin battery 46 supplies electric power to the LED 56, and the LED 56 emits light. The structure of the first circuit 43 and the second circuit 53 can be modified to a more practical structure than that of the example of FIGS. 4 and 5. For example, the second circuit 53 may have, instead of the LED 56, a circuit for measuring heart rate and another circuit for transmitting the measurement results.

According to the example of FIGS. 4 and 5, each of the number of the first contact points 48 and the number of the second contact points 58 is two. However, each of the number of the first contact points 48 and the number of the second contact points 58 may be one as shown in FIG. 2 or may be three or more. Thus, referring to FIGS. 2 and 3, the first circuit member 40 should have one or more of the first contact points 48, and the second circuit member 50 should have one or more of the second contact points 58 which correspond to the first contact points 48, respectively. In the fabricated device 10, each of the first contact points 48 should be in contact with the corresponding second contact point 58.

Hereafter, more specific explanation will be made about the device 10 of the present embodiment.

Referring to FIG. 1, the first sealing member 20 of the present embodiment has a first inner portion 22 and a first outer portion 24. Each of the first inner portion 22 and the first outer portion 24 is a part of the first film 20F. The first inner portion 22 is located inward of the first outer portion 24 in the XY-plane. In other words, the first outer portion 24 is a part of the first film 20F which surrounds the first inner portion 22.

Referring to FIG. 2, the second sealing member 30 of the present embodiment has a second inner portion 32 and a second outer portion 34. Each of the second inner portion 32 and the second outer portion 34 is a part of the second film 30F. The second inner portion 32 is located inward of the second outer portion 34 in the XY-plane. In other words, the second outer portion 34 is a part of the second film 30F which surrounds the second inner portion 32.

Referring to FIGS. 1 to 3, the first inner portion 22 of the first film 20F and the second inner portion 32 of the second film 30F of the device 10 are parts for accommodating the circuit structure 12. According to the present embodiment, before the device 10 is formed (see FIG. 7), the first film 20F extends uniformly along the XY-plane, and there is no visible boundary between the first inner portion 22 and the first outer portion 24. Before the device 10 is formed (see FIG. 7), the second film 30F extends uniformly along the XY-plane, and there is no visible boundary between the second inner portion 32 and the second outer portion 34. However, the present invention is not limited thereto. For example, a visible boundary such as a depression may be formed between the first inner portion 22 and the first outer portion 24, and a visible boundary such as a depression may be formed between the second inner portion 32 and the second outer portion 34.

Referring to FIG. 1, the first outer portion 24 of the present embodiment has a first seal portion 26 and a first contact portion 28. Referring to FIG. 2, the second outer portion 34 of the present embodiment has a second seal portion 36 and a second contact portion 38. Referring to FIGS. 1 to 3, the first seal portion 26 and the second seal portion 36 of the present embodiment are bonded together to form a seal trace 16. According to the present embodiment, the first seal portion 26 and the second seal portion 36 are bonded together by heat-sealing. Thus, the seal trace 16 of the present embodiment is a trace where the first seal portion 26 and the second seal portion 36 are welded to each other by heating. However, the present invention is not limited thereto, but the first seal portion 26 and the second seal portion 36 can be bonded together by various methods such as high frequency, ultrasonic, laser or adhesive.

Referring to FIGS. 1 and 2, the seal trace 16 of the present embodiment is formed throughout entire circumference of the first seal portion 26 and the second seal portion 36. In other words, the seal trace 16 surrounds the first inner portion 22 and the second inner portion 32 throughout their entire circumference in the XY-plane. However, the present invention is not limited thereto, but the seal trace 16 may be formed on a necessary part in accordance with the forming method of the device 10. For example, the seal trace 16 may be partially formed or may not be formed at all.

Referring to FIG. 3, as described later, the inside of the device 10 is vacuumed after the first seal portion 26 and the second seal portion 36 are bonded together. According to the present embodiment, when the inside of the device 10 is vacuumed, the first contact portion 28 and the second contact portion 38 are brought into contact with each other in a contact region 17 because of air pressure difference. As a result, the device 10 is formed with a closed space 18. The closed space 18 is enclosed by the first inner portion 22 and the second inner portion 32. The contact region 17 of the present embodiment seamlessly surrounds the first inner portion 22 and the second inner portion 32 throughout their entire circumference in the XY-plane. However, the present invention is not limited thereto, but the contact region 17 may be formed on a necessary part in accordance with the forming method of the device 10. For example, the contact region 17 may be partially formed or may not be formed at all.

The closed space 18, which is formed as described above, is enclosed by the first sealing member 20 and the second sealing member 30 and is shut off from an outer space outside the device 10. According to the present embodiment, the first seal portion 26 and the second seal portion 36 are firmly bonded together. In addition, the contact region 17 is located inward of the seal trace 16 in the XY-plane and blocks the air which might flow between the inside and the outside of the closed space 18. Thus, air pressure in the closed space 18 is kept to low pressure lower than the atmospheric pressure.

The first circuit member 40 and the second circuit member 50 are shut in the closed space 18 which is kept to the aforementioned low pressure. The first contact point 48 and the second contact point 58 are in contact with each other in the closed space 18. In detail, a contact force is generated between the first contact point 48 and the second contact point 58 because of air pressure difference between the inside and the outside of the closed space 18. The first contact point 48 and the second contact point 58 are pressed against each other because of this air pressure difference. Therefore, the contact between the first contact point 48 and the second contact point 58 can be securely kept.

Summarizing the explanation described above, the first sealing member 20 and the second sealing member 30 including the additional film 60 of the device 10 of the present embodiment overlap with each other to be in contact with each other while the first circuit member 40 and the second circuit member 50 (hereafter, simply referred to as "circuit members") are sandwiched therebetween. Each of the first sealing member 20 and the second sealing member 30 of the present embodiment is basically formed of a film. The additional film 60 can be formed by embossing a thin insulation film.

Moreover, the structure of each of the circuit members is not restricted except that each of the circuit members should be provided with a contact point such as the first contact point 48 or the second contact point 58. Thus, each of the circuit members of the present embodiment has a simple structure and can be formed of various material. For example, each of the circuit members may be an insulation film which is formed with a conductive pattern such as the first conductive pattern 44 with a contact point or the second conductive pattern 54 with a contact point. In this instance, the thickness of the entire device 10 can be made extremely thin. Thus, the present embodiment provides the new device 10 which is new and can be made thinner.

According to the present embodiment, the first seal portion 26 and the second seal portion 36 are bonded together, and the first contact portion 28 and the second contact portion 38 are in contact with each other. According to this structure, the closed space 18 can be reliably kept airtight. However, the present invention is not limited thereto. For example, the first seal portion 26 and the second seal portion 36 may partially surround the first contact portion 28 and the second contact portion 38 in the XY-plane. The first seal portion 26 and the second seal portion 36 may partially surround the first inner portion 22 and the second inner portion 32 in the XY-plane.

According to the present embodiment, the first circuit member 40 and the second circuit member 50 can be easily taken out from the closed space 18 by cutting off the first seal portion 26 and the second seal portion 36. Thus, according to the present embodiment, the members can be easily collected separately and can be reused.

Referring to FIG. 1, each of the first sealing member 20 and the second sealing member 30 of the present embodiment includes two layers consisting of a meltable layer 146 which is meltable by the heat-sealing and an unmeltable layer 148 which is not meltable by the heat-sealing. The meltable layer 146 and the unmeltable layer 148 are formed in the first film 20F. The meltable layer 146 and the unmeltable layer 148 are also formed in the second film 30F or a rigid circuit board which replaces the second film 30F. Thus, each of the first film 20F and the second film 30F of the present embodiment has a two-layer structure formed of the meltable layer 146 and the unmeltable layer 148.

For example, the meltable layer 146 is made of polyethylene, and the unmeltable layer 148 is made of nylon. According to this structure, the meltable layers 146 can be fused to each other while the unmeltable layers 148 of the first seal portion 26 and the second seal portion 36 are maintained. However, the present invention is not limited thereto, but each of the first film 20F and the second film 30F may have a structure in accordance with the sealing method. For example, each of the first film 20F and the second film 30F may include only one layer or may include three or more layers.

Each of the first film 20F and the second film 30F of the present embodiment is formed so that a part thereof, which is other than the first seal portion 26 and the second seal portion 36, also includes the meltable layer 146 and the unmeltable layer 148. However, the present invention is not limited thereto. For example, the meltable layer 146 may be formed only in each of the first seal portion 26 and the second seal portion 36.

Referring to FIG. 1, each of the first sealing member 20 and the second sealing member 30 is preferred to have a high barrier property against oxygen. More specifically, each of the first film 20F and the second film 30F is preferred to comprise a layer made of high oxygen barrier material which is material having a high barrier property against oxygen. According to this layer-structure, oxidation of the metal members of the circuit structure 12 can be reduced.

For example, the high oxygen barrier material may be linear low-density polyethylene (LLDPE). More specifically, the high oxygen barrier material may be PET/Al/PE which is formed by laminating polyethylene terephthalate, aluminum and polyethylene; ON/PE which is formed by laminating biaxially stretched nylon and polyethylene; PET/EVOH/PE which is formed by laminating polyethylene terephthalate, polyvinyl chloride and polyethylene; or may be formed by laminating a transparent high barrier film and polyethylene. The transparent high barrier film may be polyethylene terephthalate (PET) deposited with SiOx or aluminum oxide.

Each of the first sealing member 20 and the second sealing member 30 of the present embodiment is preferred to have a high barrier property against water vapor in addition to the high barrier property against oxygen. More specifically, each of the first film 20F and the second film 30F is preferred to comprise a layer made of high water-vapor barrier material which is material having a high barrier property against water vapor. According to this layer-structure, the circuit structure 12 can be water-proofed. For example, the high water-vapor barrier material may be material which is a sheet made of ON/PE, biaxially stretched polypropylene (OPP) or PET and is coated with polyvinylidene chloride (PVDC).

Each of the first sealing member 20 and the second sealing member 30 may have various barrier properties such as a barrier property against nitrogen in addition to the high barrier property against oxygen and the high barrier property against water vapor. Thus, each of the first sealing member 20 and the second sealing member 30 is preferred to have high barrier properties in accordance with its use.

Figure 6:
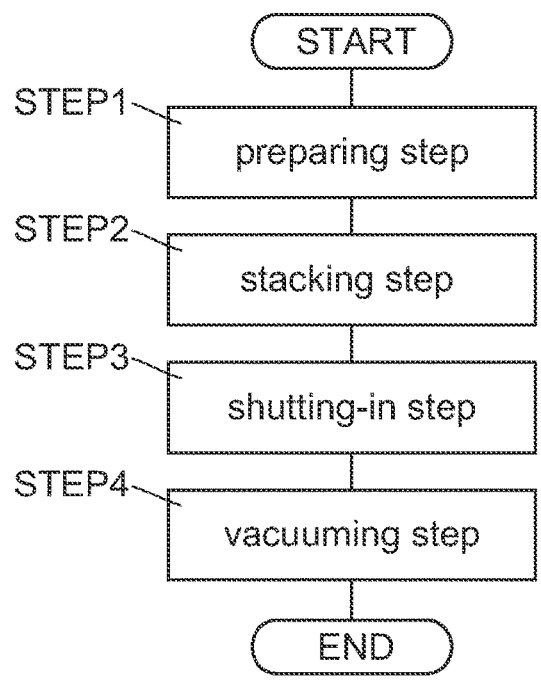
FIG. 6 is a flowchart showing an example of a forming method for forming the device of FIG. 1.

Referring to FIG. 6, the device 10 (see FIG. 1) of the present embodiment is formed via four steps consisting of a preparing step (STEP 1), a stacking step (STEP 2), a shutting-in step (STEP 3) and a vacuuming step (STEP 4).

However, the present invention is not limited thereto, but the forming method of the device 10 can be modified as necessary. Hereafter, explanation will be made about the forming method of the device 10 of the present embodiment.

Referring to FIG. 7, in the preparing step (see FIG. 6), a device material set 11 is prepared. The device material set 11 comprises the first sealing member 20, the second sealing member 30, the first circuit member 40 and the second circuit member 50. The first sealing member 20 basically comprises the first film 20F and comprises the air valve 70 provided on the first film 20F. The second sealing member 30 basically comprises the second film 30F and comprises the additional film 60 formed with the uneven portion 62. The first circuit member 40 comprises the first contact point 48. The second circuit member 50 comprises the second contact point 58.

Figure 9:
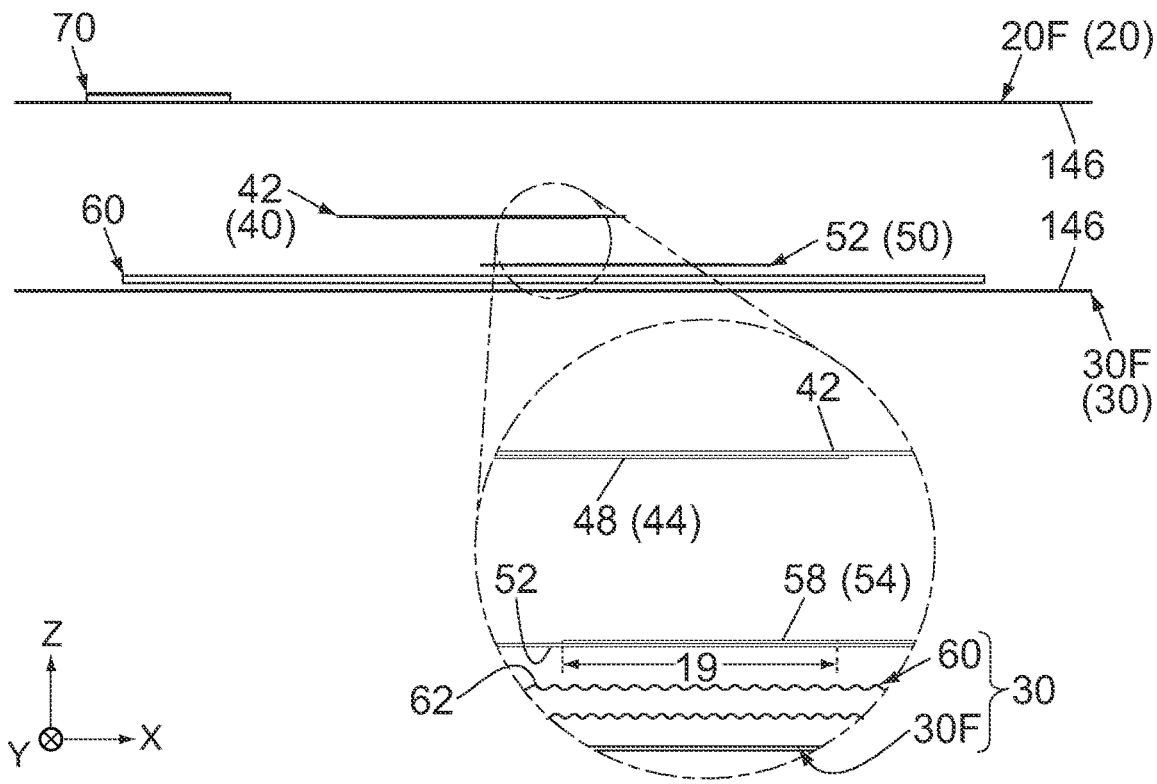
FIG. 9 is a side view showing the device material set of FIG. 7, wherein a part of the device material set enclosed by chain dotted lines is enlarged and illustrated.

Then, referring to FIGS. 7 and 9, in the stacking step (see FIG. 6), the first sealing member 20, the first circuit member 40, the second circuit member 50 and the second sealing member 30 are stacked on each other in this order from top to bottom along the Z-direction. Meanwhile, the first circuit member 40 and the second circuit member 50 are arranged so that the first contact point 48 and the second contact point 58 face each other in the Z-direction. The additional film 60 is located at the middle of second film 30F in the XY-plane. The first circuit member 40 and the second circuit member 50 are located at the middle of the additional film 60 in the XY-plane. In addition, the first film 20F and the second film 30F are arranged so that two of the meltable layers 146 thereof face each other in the Z-direction.

Referring to FIG. 9, the uneven portion 62 of the additional film 60 which is arranged as describe above faces the second circuit member 50 in the Z-direction. The uneven portion 62 covers a predetermined region 19, which corresponds to the second contact point 58, from below. In other words, the uneven portion 62 covers the negative Z-side of the predetermined region 19. The predetermined region 19 of the present embodiment is a part of a lower surface of the second base portion 52 of the second circuit member 50 which is located just under the second contact point 58.

Figure 10:
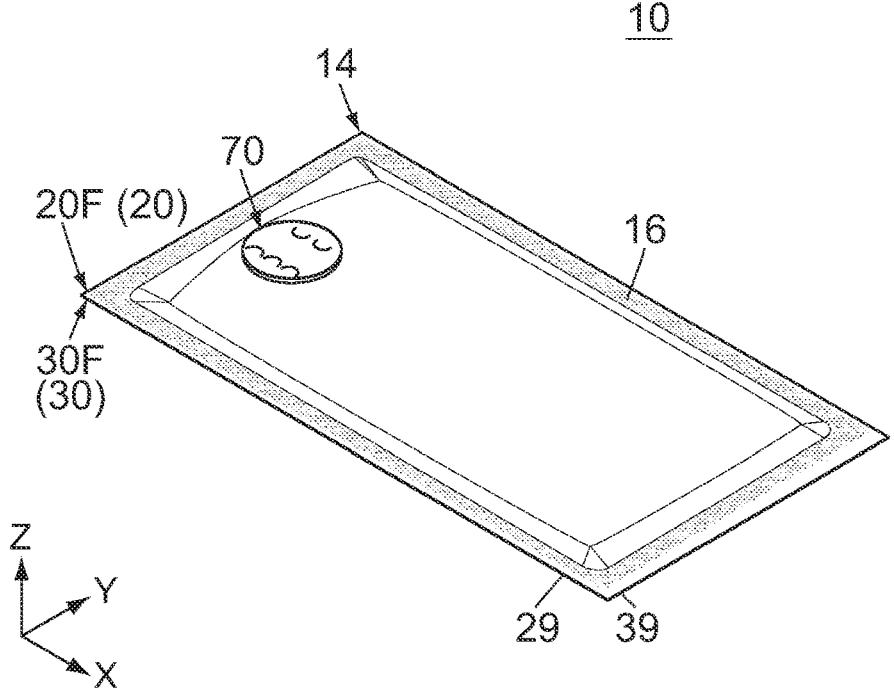
FIG. 10 is a perspective view showing the device in a shutting-in step of the forming method of FIG. 6.

Then, referring to FIGS. 9 and 10, in the shutting-in step (see FIG. 6), heat-sealing is applied to the first film 20F and the second film 30F. In detail, parts of the two meltable layers 146, which are located at outer circumferences of the first film 20F and the second film 30F in the XY-plane, are welded to each other via heat-sealing.

Figure 11:
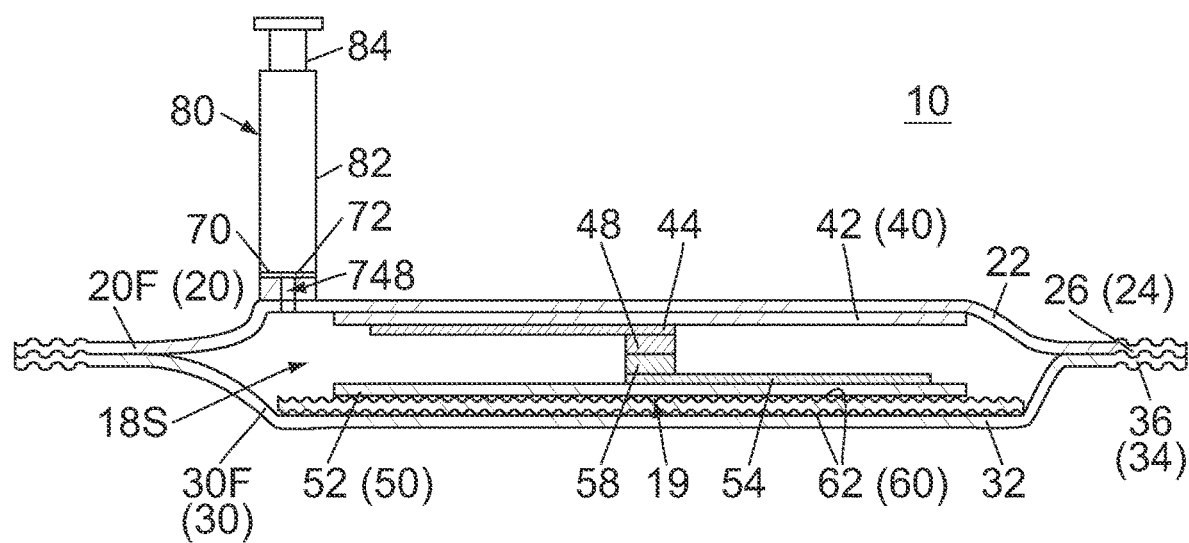
FIG. 11 is a schematic, cross-sectional view showing the device of FIG. 10, taken along line III-III of FIG. 1, wherein a side surface of a vacuum instrument is illustrated, the inner structure of the device is merely schematically illustrated, and the size and arrangement of each member are not equal to the actual size and arrangement thereof.

Referring to FIG. 11 together with FIG. 10, as a result of the heat-sealing, the device 10 is formed with the seal trace 16 and an inner space 18S located therein. The seal trace 16 is formed on outer circumferences of the first film 20F and the second film 30F in the XY-plane so as to continuously and seamlessly extends. Thus, the inner space 18S is enclosed by the first sealing member 20 and the second sealing member 30 and is shut off from the outside of the device 10 except for the air valve 70. The first circuit member 40 and the second circuit member 50 are shut in the inner space 18S together with the additional film 60 of the second sealing member 30.

Then, in the vacuuming step (see FIG. 6), the inner space 18S is vacuumed. According to the present embodiment, the air valve 70 and an instrument 80 are used to discharge the air out of the inner space 18S. The instrument 80 of the present embodiment is a syringe-type piston pump. The instrument 80 comprises a syringe 82 and a plunger 84. The syringe 82 has a lower end which has a ring shape in the XY-plane. The ring shape of the syringe 82 corresponds to the outer circumference of the cover portion 72 of the air valve 70.

In the vacuuming step, first, the lower end of the syringe 82 is pressed against the upper surface of the cover portion 72. Then, the plunger 84 is pulled upward. Meanwhile, the air valve 70 takes the open state, and an air passage is formed between the inner space 18S and the inside of the syringe 82. The air in the inner space 18S is discharged into the inside of the syringe 82 through the passing hole 748 and the cuts 724 (see FIG. 9) of the air valve 70. As a result, air pressure of the inner space 18S is gradually lowered. When air pressure of the inner space 18S becomes low pressure close to that of a vacuum, the vacuuming by using the instrument 80 is stopped.

When the vacuuming is stopped, the valves 722 (see FIG. 9) of the air valve 70 cover the cuts 724 (see FIG. 9) because of air pressure difference between air pressure of the inner space 18S and the atmospheric pressure, and thereby the air valve 70 takes the closed state. As a result, air pressure in the inner space 18S is kept to low pressure. Thus, the device 10 is formed with the closed space 18 (see FIG. 3). The closed space 18 is the inner space 18S which is shut off from the outside and has the low pressure. The first contact point 48 and the second contact point 58 are pressed against each other and are brought into contact with each other because of air pressure difference between the inside and the outside of the closed space 18.

Referring to FIG. 11 together with FIG. 3, the first film 20F and the second film 30F tend to be in close contact with each other upon vacuuming, and thereby tend to form a close contact region such as the contact region 17. If the additional film 60 is not provided, the close contact region of the first film 20F and the second film 30F will be formed between the air valve 70 and the predetermined region 19. The thus-formed close contact region might block an air passage between the air valve 70 and the predetermined region 19. As a result, air pressure of a space in which the first contact point 48 and the second contact point 58 are located might be insufficiently lowered, and thereby the first contact point 48 and the second contact point 58 might be unreliably brought into contact with each other.

In contrast, since the additional film 60 of the present embodiment is located between the first film 20F and the second film 30F, direct contact between the first film 20F and the second film 30F is prevented. Moreover, since the additional film 60 has the uneven portion 62, the air passage between the air valve 70 and the predetermined region 19 can be kept even in a case where the first film 20F and the second film 30F are indirectly brought into contact with each other via the additional film 60. Thus, the uneven portion 62 of the present embodiment prevents formation of the close contact region which might block the air passage between the air valve 70 and the predetermined region 19. Therefore, the first contact point 48 and the second contact point 58 can be reliably brought into contact with each other.

Referring to FIG. 2 together with FIG. 3, the uneven portion 62 of the present embodiment is shut in the closed space 18 and entirely covers a region which corresponds to the closed space 18. However, the present invention is not limited thereto. From a viewpoint of reliable contact between the first contact point 48 and the second contact point 58 upon vacuuming, the uneven portion 62 may continuously cover only a region which extends from the air valve 70 to the predetermined region 19. In particular, the uneven portion 62 may continuously cover only a region which extends from the predetermined region 19 to the passing hole 748 which is an air passage in the air valve 70. In an instance where a distance between the air valve 70 and the predetermined region 19 is short, the uneven portion 62 may cover only the predetermined region 19 which corresponds to at least one of the first contact point 48 and the second contact point 58.

However, when the uneven portion 62 has a small size in the XY-plane, an air pool may be formed at a position which is apart from the predetermined region 19 during vacuuming. The air pool may be surrounded by the close contact region where the first film 20F and the second film 30F are in close contact with each other. In an instance where such an air pool is formed, air might flow from the air pool to the predetermined region 19 when the device 10 is used. As a result, air pressure of the predetermined region 19 might be made higher. Therefore, the uneven portion 62 is preferred to entirely cover a region which corresponds to the closed space 18 as disclosed in the present embodiment.

Referring to FIG. 3, the additional film 60 of the present embodiment is an embossed film distinct and separable from the second film 30F and is arranged on the second film 30F. The uneven portion 62 is formed over upper and lower surfaces of the additional film 60. However, the present invention is not limited thereto. For example, the additional film 60 may be adhered to and fixed on an upper surface of the second film 30F. The uneven portion 62 may be formed only on the upper surface of the additional film 60. The second film 30F may be embossed so as to be formed with the uneven portion 62. In this instance, the additional film 60 does not need to be provided. Thus, the second sealing member 30 may comprise only the second film 30F which has the uneven portion 62.

The additional film 60 of the present embodiment forms the second sealing member 30 together with the second film 30F. However, the present invention is not limited thereto. For example, the additional film 60 may form the first sealing member 20 together with the first film 20F. More specifically, the additional film 60 may be arranged under the first film 20F. In this instance, the uneven portion 62 covers the predetermined region 19, which corresponds to the first contact point 48, from above. The thus-covered predetermined region 19 is a part of an upper surface of the first base portion 42 of the first circuit member 40 which is located just over the first contact point 48. Moreover, the first film 20F may be embossed so as to be formed with the uneven portion 62. In this instance, the additional film 60 does not need to be provided.

The device 10 of the present embodiment comprises only one of the uneven portions 62. However, the present invention is not limited thereto. Each of the first sealing member 20 and the second sealing member 30 may be provided with the uneven portion 62. More specifically, each of the first sealing member 20 and the second sealing member 30 may be provided with one of the additional films 60. Instead, each of the first film 20F and the second film 30F may be formed with the uneven portion 62.

In consideration of the modifications described above, at least one of the first sealing member 20 and the second sealing member 30 may comprise the additional film 60. Moreover, the additional film 60 does not have to be provided. Thus, at least one of the first sealing member 20 and the second sealing member 30 may be provided with the uneven portion 62. The uneven portion 62 may be in contact with at least one of the first circuit member 40 and the second circuit member 50.

Summarizing the forming method of the device 10 in consideration of the modifications described above, the forming method of the device 10 comprises preparing the first sealing member 20, the second sealing member 30, the first circuit member 40 and the second circuit member 50, the first sealing member 20 basically comprising the first film 20F formed of a film, the first film 20F being provided with the air valve 70, at least one of the first sealing member 20 and the second sealing member 30 being provided with the uneven portion 62, the first circuit member 40 comprising the first contact point 48, the second circuit member 50 comprising the second contact point 58.

Moreover, the forming method of the device 10 comprises stacking the first sealing member 20, the first circuit member 40, the second circuit member 50 and the second sealing member 30 on each other in this order, the first contact point 48 and the second contact point 58 facing each other, the uneven portion 62 facing at least one of the first circuit member 40 and the second circuit member 50, the uneven portion 62 covering the predetermined region 19 which corresponds to at least one of the first contact point 48 and the second contact point 58.

Moreover, the forming method of the device 10 comprises shutting the first circuit member 40 and the second circuit member 50 in the inner space 18S (see FIG. 11) which is formed in the device 10, the inner space 18S being enclosed by the first sealing member 20 and the second sealing member 30 and being shut off from the outer space outside the device 10 except for the air valve 70.

Moreover, the forming method of the device 10 comprises vacuuming the inner space 18S (see FIG. 11) by using the air valve 70 so that the first contact point 48 and the second contact point 58 are brought into contact with each other.

Referring to FIG. 3, according to the forming method of the present embodiment, the first contact point 48 and the second contact point 58 are securely in contact with each other without using a fixing member such as an adhesive. Therefore, when the device 10 is no longer used, the device 10 can be disassembled merely by cutting off the first outer portion 24 and the second outer portion 34. In addition, the first circuit member 40 and the second circuit member 50 can be shut in the closed space 18 having low pressure, so that degradation of the metal members due to oxidation can be reduced, for example.

Referring to FIG. 11, according to the forming method of the present embodiment, the simple instrument 80 can be used for easy vacuuming. The vacuuming by the instrument 80 can be repeatedly performed. For example, even when air pressure in the closed space 18 is made higher during use of the device 10, the instrument 80 can be used for vacuuming again. Therefore, the contact force between the first contact point 48 and the second contact point 58 can be kept during use of the device 10. However, the present invention is not limited thereto, but the forming method of the device 10 can be modified as necessary.

For example, the structure of the instrument 80 is not specifically limited, provided that it can be used for vacuuming. A nozzle may be used instead of the illustrated instrument 80. The nozzle may be inserted into and vacuum the device 10. In this instance, the air valve 70 does not need to be provided. Alternatively, a commercially available desktop vacuum packaging machine (not shown) may be used for sealing and vacuuming. Referring to FIG. 7, the device material set 11 may be arranged in a chamber (not shown) so that vacuuming is performed simultaneously with heat-sealing. However, by using a commercially available, simple instrument such as the instrument 80 (see FIG. 11), the device 10 can be easily formed, and the contact force between the first contact point 48 and the second contact point 58 can be easily kept.

Referring to FIG. 3, a pressure sensing member (not shown), which can visibly show air pressure in the closed space 18, may be shut in the closed space 18. For example, the pressure sensing member may be a pressure measuring film which emits various colors depending on air pressure. Instead, the pressure sensing member may be elastically deformable cushioning material such as a urethane sponge. When the cushioning material is uses as the pressure sensing member, air pressure in the closed space 18 can be estimated by visual recognition of the thickness of the cushioning material. The cushioning material may be arranged so as to press the first contact point 48 or the second contact point 58. In a case where the first circuit member 40 or the second circuit member 50 has a sufficiently visible thickness, air pressure in the closed space 18 can be estimated without using the pressure sensing member. For example, referring to FIGS. 1 and 10, air pressure in the closed space 18 can be estimated by visually recognizing the change in shape of a part of the first film 20F which is located in the vicinity of a side of the first circuit member 40 or a part of the second film 30F which is located in the vicinity of a side of the second circuit member 50.

The present embodiment can be further variously modified in addition to the already described modifications. Hereafter, explanation will be made about four modifications.

Figure 12:
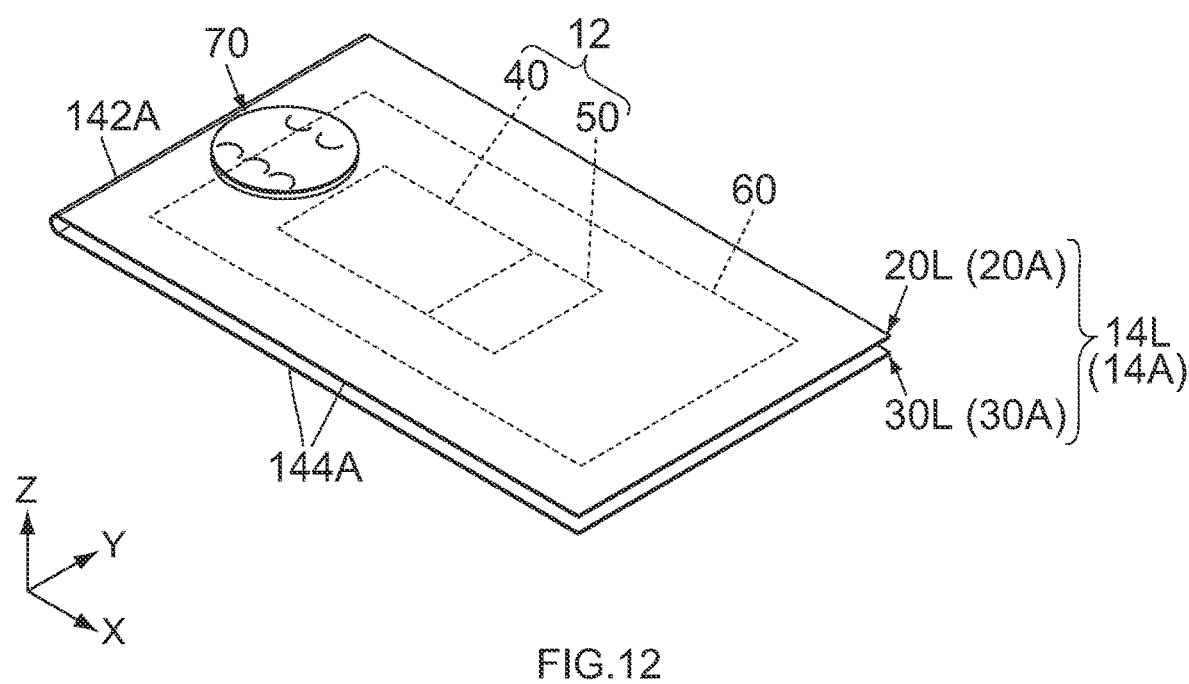
FIG. 12 is a perspective view showing a modification of the device material set of FIG. 7, wherein outlines of the hidden first circuit member, the hidden second circuit member and a hidden additional film are illustrated with dashed line.
Figure 13:
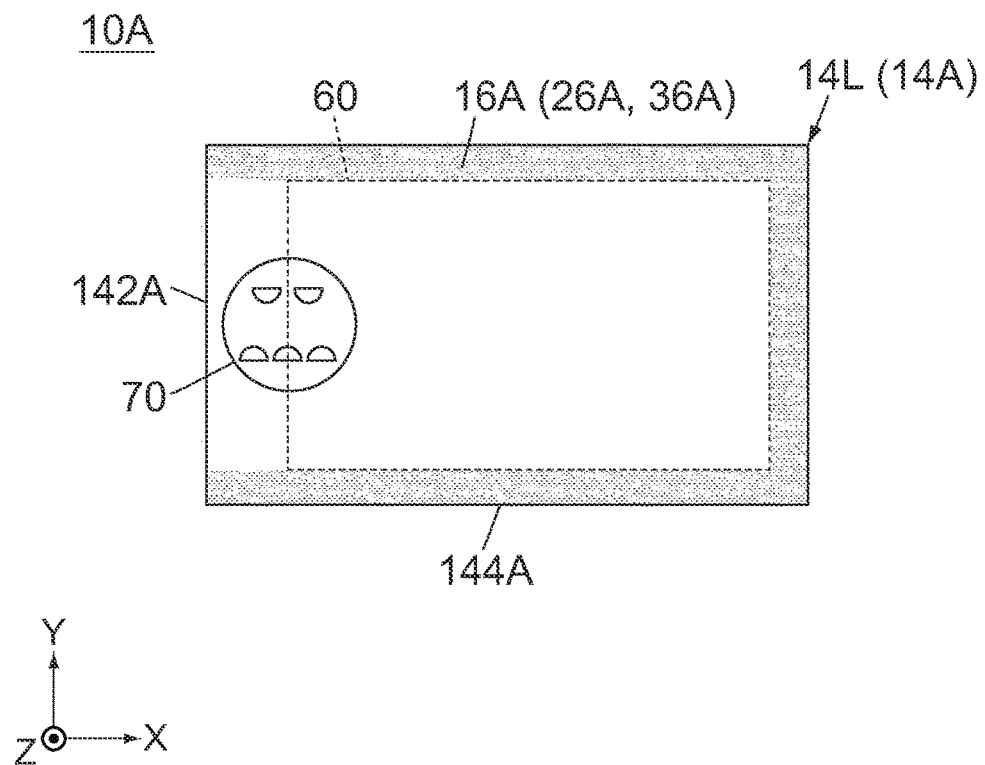
FIG. 13 is a top view showing a device formed of the device material set of FIG. 12, wherein an outline of the hidden additional film is illustrated with dashed line.

Referring to FIGS. 12 and 13, a device 10A according to a first modification is formed from a device material set 11A. Comparing FIG. 12 with FIG. 7, the device material set 11A comprises a sealing member 14A different from the sealing member 14 of the device material set 11 and comprises the circuit structure 12 same as that of the device material set 11. The sealing member 14A comprises one film member (planar sheet) 14L made of insulator, the additional film 60 and the air valve 70. The circuit structure 12 comprises the first circuit member 40 and the second circuit member 50. Thus, the device 10A comprises the first circuit member 40 and the second circuit member 50.

Referring to FIG. 12, the planar sheet 14L is bent at the middle thereof, namely a predetermined portion 142A, in a front-rear direction (X-direction) so as to be formed with a first film (sheet piece) 20L and a second film (sheet piece) 30L which overlap with each other in the Z-direction. Thus, the first film 20L and the second film 30L are two sheet pieces of the single film member 14L which overlap with each other. The film member 14L is a single planar sheet which has the predetermined portion 142A and a peripheral edge 144A. The peripheral edge 144A is an edge of the film member 14L in the XY-plane.

Referring to FIGS. 12 and 13, the device 10A comprises a first sealing member 20A and a second sealing member 30A similar to those of the device 10 (see FIG. 1). The first sealing member 20A basically comprises the first film 20L and comprises the air valve 70 provided on the first film 20L. The second sealing member 30A basically comprises the second film 30L and comprises the additional film 60.

The device 10A of the present modification can be formed by a forming method similar to that of the device 10 (see FIG. 1). For example, in the stacking step (see FIG. 6), the circuit structure 12 is arranged between the first sealing member 20A and the second sealing member 30A in the Z-direction. The additional film 60 is arranged between the second film 30L and the circuit structure 12 in the Z-direction.

The device 10A has a structure similar to that of the device 10 (see FIG. 1). For example, a first seal portion 26A and a second seal portion 36A are bonded together to form a seal trace 16A. The device 10A is formed with the closed space 18 (see FIG. 3) which is enclosed by the first sealing member 20A and the second sealing member 30A. The first circuit member 40, the second circuit member 50 and the additional film 60 are shut in the closed space 18. The first contact point 48 (see FIG. 3) of the first circuit member 40 and the second contact point 58 (see FIG. 3) of the second circuit member 50 are in contact with each other.

However, the device 10A is different from the device 10 (see FIG. 1) in the following points. First, the first film 20L and the second film 30L are the two sheet pieces which are folded at the predetermined portion 142A to overlap with each other. Thus, the first film 20L and the second film 30L are connected to each other at the predetermined portion 142A. According to this structure, there is no need to seal the part between the predetermined portion 142A and the closed space 18 (see FIG. 3). Accordingly, only the part between the closed space 18 and the peripheral edge 144A is sealed. In other words, the seal trace 16A is formed only between the closed space 18 and the peripheral edge 144A.

Figure 14:
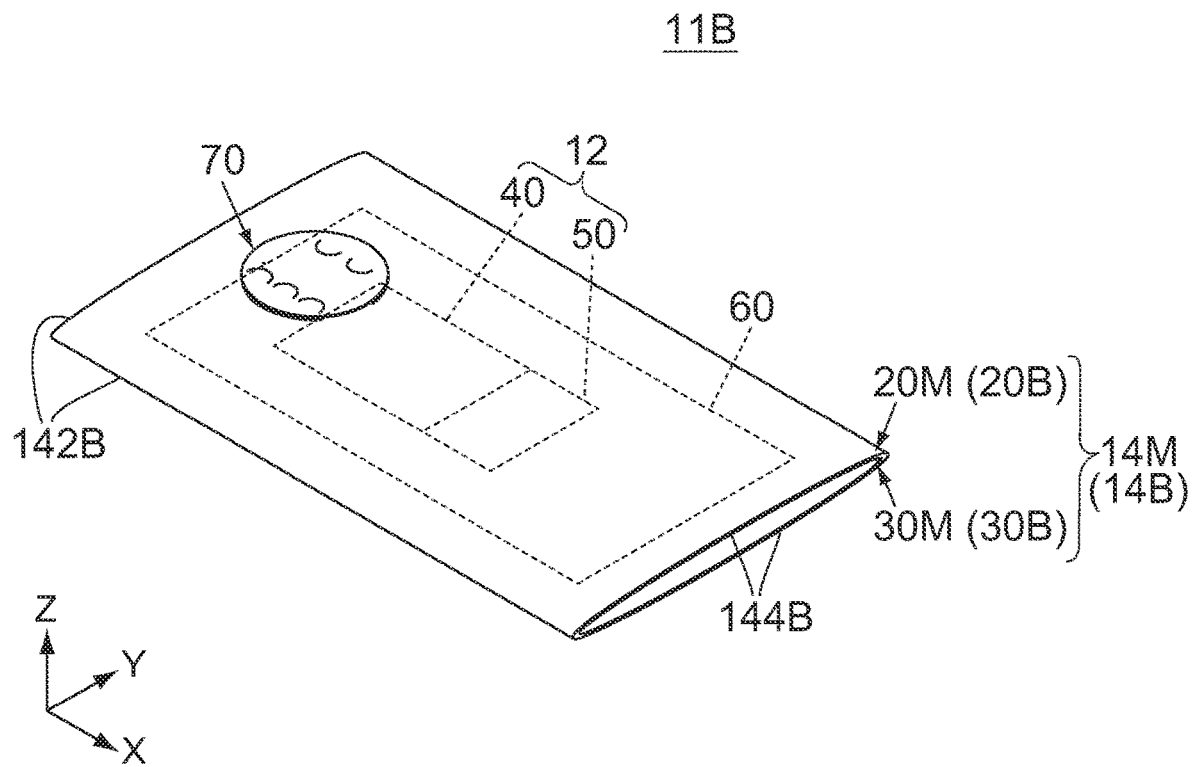
FIG. 14 is a perspective view showing another modification of the device material set of FIG. 7, wherein outlines of the hidden first circuit member, the hidden second circuit member and the hidden additional film are illustrated with dashed line.
Figure 15:
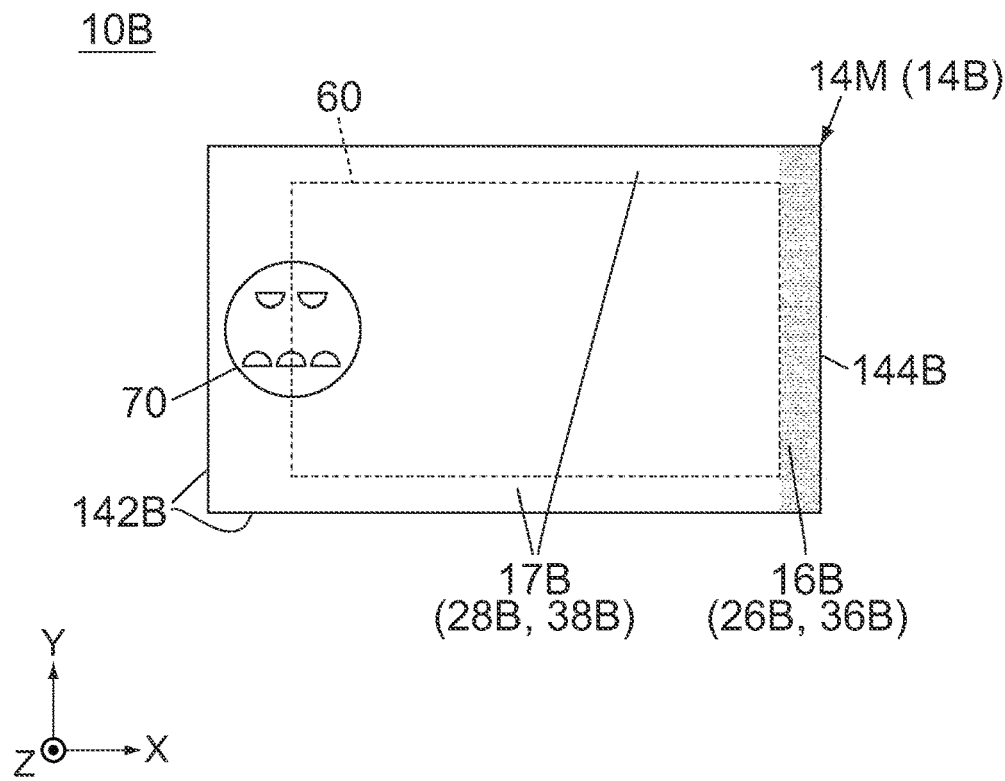
FIG. 15 is a top view showing a device formed of the device material set of FIG. 14, wherein an outline of the hidden additional film is illustrated with dashed line.

Referring to FIGS. 14 and 15, a device 10B according to a second modification is formed from a device material set 11B. Comparing FIG. 14 with FIG. 7, the device material set 11B comprises a sealing member 14B different from the sealing member 14 of the device material set 11 and comprises the circuit structure 12 same as that of the device material set 11. The sealing member 14B comprises one film member (folder-like sheet) 14M made of insulator, the additional film 60 and the air valve 70. The circuit structure 12 comprises the first circuit member 40 and the second circuit member 50. Thus, the device 10B comprises the first circuit member 40 and the second circuit member 50.

Referring to FIG. 14, the folder-like sheet 14M has three connected sides, namely a predetermined portion 142B, in the XY-plane and opens at a front end (positive X-side end) thereof. According to this structure, the folder-like sheet 14M is formed with a first film (sheet piece) 20M and a second film (sheet piece) 30M which overlap with each other in the Z-direction. Thus, the first film 20M and the second film 30M are two sheet pieces of the single film member 14M which overlap with each other. The film member 14M is a single folder-like sheet which has the predetermined portion 142B and a peripheral edge 144B. The peripheral edge 144B is an edge of the opening of the film member 14M.

Referring to FIGS. 14 and 15, the device 10B comprises a first sealing member 20B and a second sealing member 30B similar to those of the device 10 (see FIG. 1). The first sealing member 20B basically comprises the first film 20M and comprises the air valve 70 provided on the first film 20M. The second sealing member 30B basically comprises the second film 30M and comprises the additional film 60.

The device 10B of the present modification can be formed by a forming method similar to that of the device 10 (see FIG. 1). For example, in the stacking step (see FIG. 6), the circuit structure 12 is put into the film member 14M and is arranged between the first sealing member 20B and the second sealing member 30B in the Z-direction. The additional film 60 is arranged between the second film 30M and the circuit structure 12 in the Z-direction.

The device 10B has a structure similar to that of the device 10 (see FIG. 1). For example, a first seal portion 26B and a second seal portion 36B are bonded together to form a seal trace 16B. A first contact portion 28B and a second contact portion 38B are in contact with each other in a contact region 17B. The device 10B is formed with the closed space 18 (see FIG. 3) which is enclosed by the first sealing member 20B and the second sealing member 30B. The first circuit member 40, the second circuit member 50 and the additional film 60 are shut in the closed space 18. The first contact point 48 (see FIG. 3) of the first circuit member 40 and the second contact point 58 (see FIG. 3) of the second circuit member 50 are in contact with each other.

However, the device 10B is different from the device 10 (see FIG. 1) in the following points. First, the first film 20M and the second film 30M are the two sheet pieces which are connected to each other at the predetermined portion 142B. Thus, the first film 20M and the second film 30M are connected to each other at the predetermined portion 142B. According to this structure, there is no need to seal the part between the predetermined portion 142B and the closed space 18 (see FIG. 3). Accordingly, only the part between the closed space 18 and the peripheral edge 144B is sealed. In other words, the seal trace 16B is formed only between the closed space 18 and the peripheral edge 144B.

Figure 16:
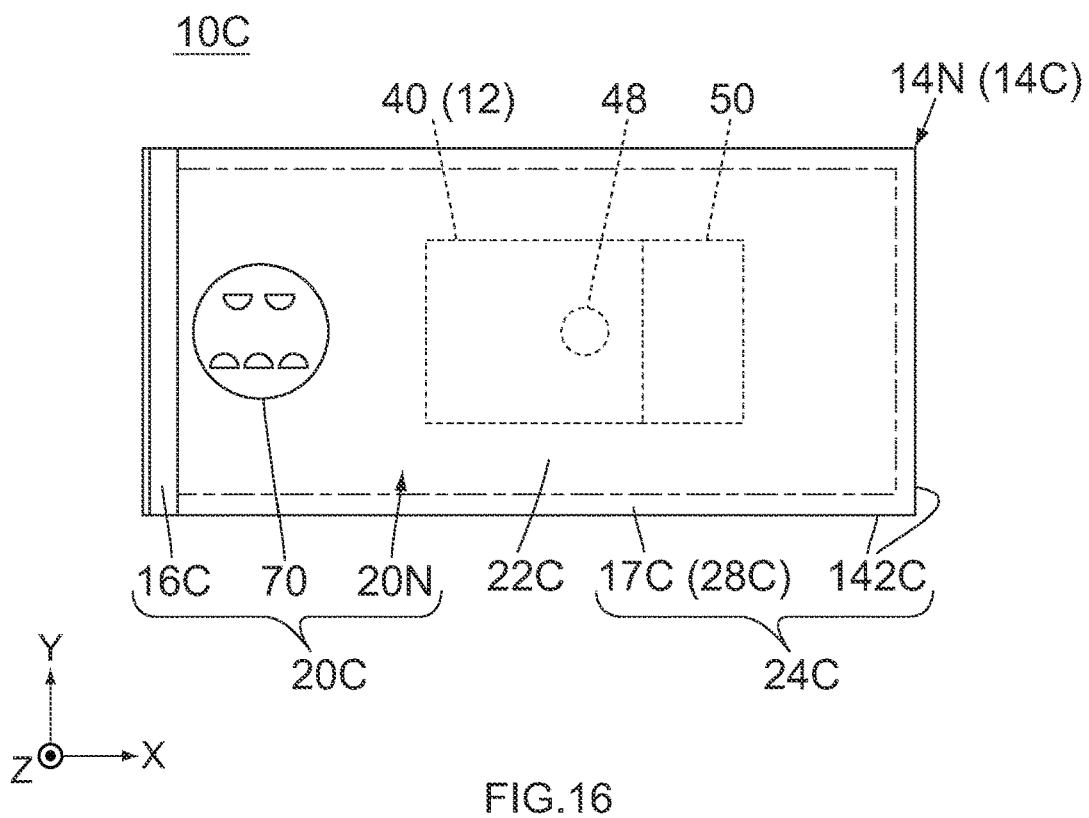
FIG. 16 is a top view showing a modification of the device of FIG. 15, wherein an outline of the hidden first circuit member and the hidden second circuit member are illustrated with dashed line, and a boundary line of the contact region is illustrated with chain dotted lines.
Figure 17:
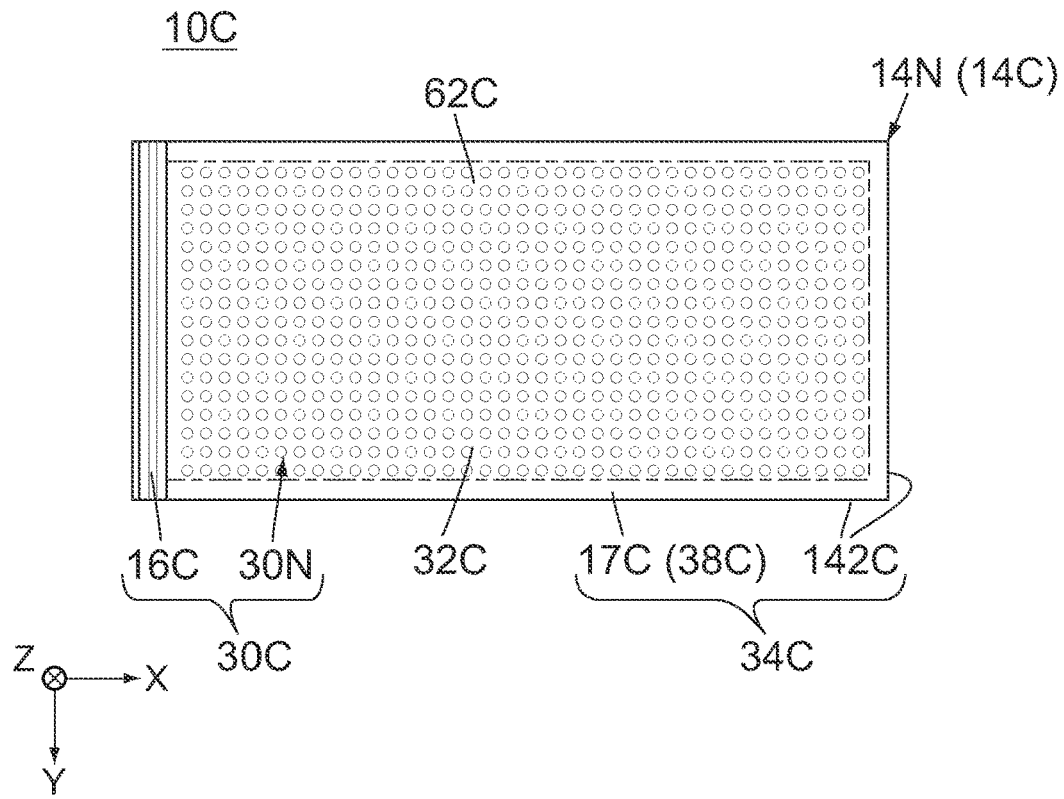
FIG. 17 is a bottom view showing the device of FIG. 16, wherein a boundary line of the contact region is illustrated with chain dotted lines.

Comparing FIGS. 16 and 17 with FIGS. 14 and 15, a device 10C according to a third modification comprises a sealing member 14C different from the sealing member 14B of the device 10B and comprises the first circuit member 40 and the second circuit member 50 same as those of the device 10B. The sealing member 14C comprises one film member (folder-like sheet) 14N made of insulator, a fastener 16C provided on an opening of the folder-like sheet 14N and the air valve 70 provided on the folder-like sheet 14N. The sealing member 14C does not comprise the additional film 60.

The folder-like sheet 14N has a first film (sheet piece) 20N and a second film (sheet piece) 30N which overlap with each other in the Z-direction similarly to the folder-like sheet 14M. The folder-like sheet 14N has a side which is provided with the fastener 16C. The first film 20N and the second film 30N are connected to each other at three sides, namely a predetermined portion 142C, on which the fastener 16C is not provided.

The device 10C comprises a first sealing member 20C and a second sealing member 30C. The first sealing member 20C basically comprises the first film 20N. In addition, the first sealing member 20C comprises the air valve 70 and an upper part (positive Z-side part) of the fastener 16C which are provided on the first film 20N. The second sealing member 30C basically comprises the second film 30N and comprises a lower part (negative Z-side part) of the fastener 16C provided on the second film 30N.

The second sealing member 30C differs from the second sealing member 30B in that the additional film 60 is not provided. Instead, the second film 30N is formed with an uneven portion 62C. The uneven portion 62C is continuously formed over the substantially entire second film 30N. However, the present invention is not limited thereto, but the second sealing member 30C may comprise the additional film 60 similar to that of the second sealing member 30B. In this instance, the second film 30N does not need to be formed with the uneven portion 62C.

The first sealing member 20C of the device 10C has a first inner portion 22C and a first outer portion 24C. The first inner portion 22C is located inward of the first outer portion 24C. The second sealing member 30C has a second inner portion 32C and a second outer portion 34C. The second inner portion 32C is located inward of the second outer portion 34C. The closed space 18 (see FIG. 3) is enclosed by the first inner portion 22C and the second inner portion 32C. The first outer portion 24C has a first contact portion 28C. The second outer portion 34C has a second contact portion 38C. The first contact portion 28C and the second contact portion 38C are in contact with each other in a contact region 17C. The uneven portion 62C entirely covers a region which corresponds to the closed space 18.

The device 10C of the present modification can be formed by a forming method similar to that of the device 10B. For example, in the stacking step (see FIG. 6), the circuit structure 12 is arranged between the first sealing member 20C and the second sealing member 30C in the Z-direction. However, the additional film 60 is not arranged. In the shutting-in step (see FIG. 6), heat-sealing is not applied to the folder-like sheet 14N, but the fastener 16C is merely closed. Therefore, the device 100 is formed with no seal trace.

Figure 18:
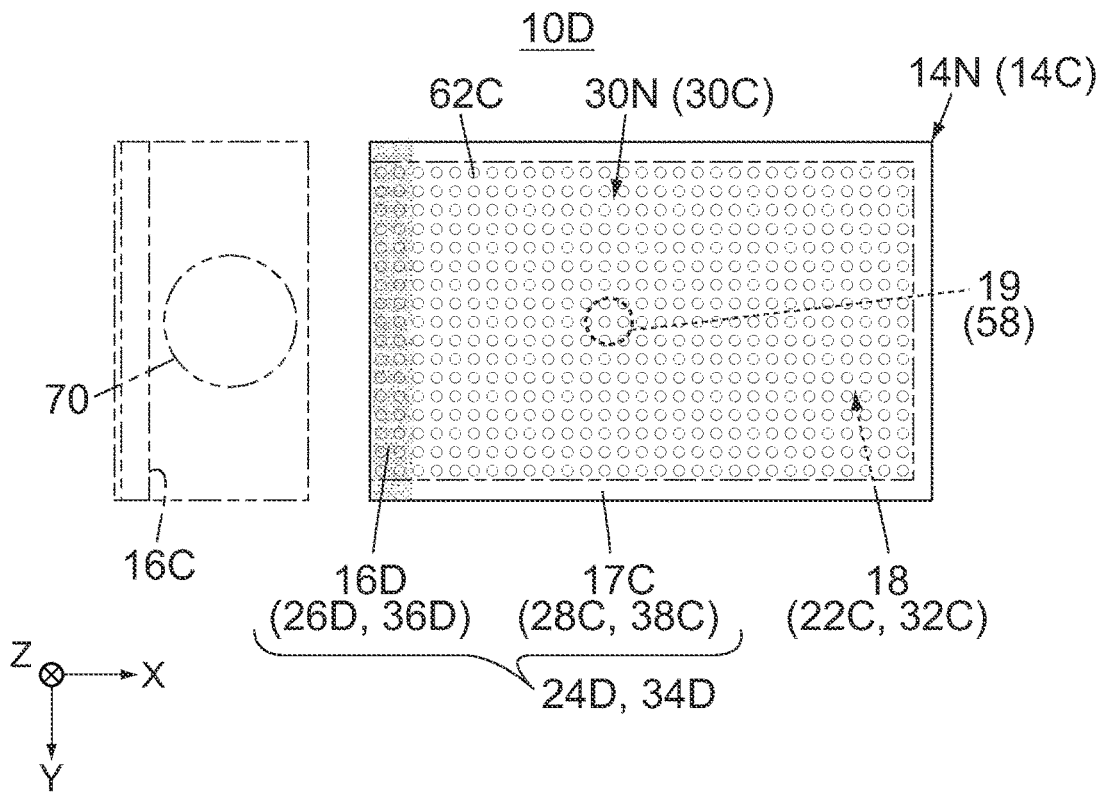
FIG. 18 is a bottom view showing a device formed by cutting out a part of the device of FIG. 17, wherein an outline of the cut part including a hidden air valve is illustrated with two-dot chain line, an outline of a hidden predetermined region which corresponds to the second contact point is illustrated with dashed line, and a boundary line of the contact region is illustrated with chain dotted lines.

Comparing FIG. 18 with FIGS. 16 and 17, a device 10D according to a fourth modification is formed from the device 10C. In detail, after the formation of the device 10C, heat-sealing is applied to the device 10C to form a seal trace 16D. Then, a part of the device 10C which is located between the seal trace 16D and the air valve 70 is cut so that the part provided with the air valve 70 is detached. As a result, the device 10D is formed.

The first sealing member 20C of the device 10D does not comprise the air valve 70 but has the first inner portion 22C and a first outer portion 24D. The first inner portion 22C is located inward of the first outer portion 24D. The second sealing member 30C has the second inner portion 32C and a second outer portion 34D. The second inner portion 32C is located inward of the second outer portion 34D. The closed space 18 is enclosed by the first inner portion 22C and the second inner portion 32C. The first outer portion 24D has a first seal portion 26D in addition to the first contact portion 28C. The second outer portion 34D has a second seal portion 36D in addition to the second contact portion 38C.

The first seal portion 26D and the second seal portion 36D are bonded together to form the seal trace 16D. The uneven portion 62C continuously covers a region which extends from the seal trace 16D to the predetermined region 19. The predetermined region 19 corresponds to the second contact point 58. The closed space 18 of the device 10D is completely shut off from an outer space outside the device 10D. By cutting out the air valve 70 from the sealed device 10D, airtightness of the closed space 18 can be improved.

In the aforementioned four modifications, the film member is one planar sheet or one folder-like sheet. However, the film member according to the present invention is not limited thereto but can be variously modified.

Referring to FIG. 3, the first circuit member 40 of the present embodiment is a member distinct and separable from the first sealing member 20 and is not fixed to the first film 20F by a method such as adhesive. The second circuit member 50 of the present embodiment is a member distinct and separable from the second sealing member 30 and is not fixed to the additional film 60 by a method such as adhesive. However, the present invention is not limited thereto. As described below, the first circuit member 40 may be a member integral to the first sealing member 20, and the second circuit member 50 may be a member integral to the second sealing member 30.

For example, the first circuit member 40 may be provided on the first film 20F. More specifically, the first base portion 42 may be adhered to and fixed on a lower surface of the first film 20F. Instead, the first conductive pattern 44 may be formed on the lower surface of the first film 20F. Thus, the first contact point 48 may be provided on the lower surface of the first film 20F. When the first film 20F has the uneven portion 62, the first contact point 48 may be provided on the uneven portion 62. Moreover, when the first sealing member 20 comprises the additional film 60, the first base portion 42 may be adhered to and fixed on a lower surface of the additional film 60. Instead, the first conductive pattern 44 may be formed on the lower surface of the additional film 60. Thus, the first contact point 48 may be provided on the lower surface of the additional film 60.

For example, the second circuit member 50 may be provided on the additional film 60. More specifically, the second base portion 52 may be adhered to and fixed on the upper surface of the additional film 60. Instead, the second conductive pattern 54 may be formed on the upper surface of the additional film 60. Thus, the second contact point 58 may be provided on the upper surface of the additional film 60. Moreover, when the second sealing member 30 does not comprise the additional film 60, the second base portion 52 may be adhered to and fixed on the upper surface of the second film 30F. Instead, the second conductive pattern 54 may be formed on the upper surface of the second film 30F. Thus, the second contact point 58 may be provided on the upper surface of the second film 30F. When the second film 30F has the uneven portion 62, the second contact point 58 may be provided on the uneven portion 62.

In addition to the aforementioned modifications, one of the first circuit member 40 and the second circuit member 50 may be a single electronic component as previously described. Hereafter, specific explanation will be made about this example (Example 1) and Examples 2 to 4 with reference to FIGS. 19 to 22. The first circuit member 40 of Example 2 is a member integral to the first sealing member 20. The second circuit member 50 of each of Examples 3 and 4 is a member integral to the second sealing member 30.

Figure 19:
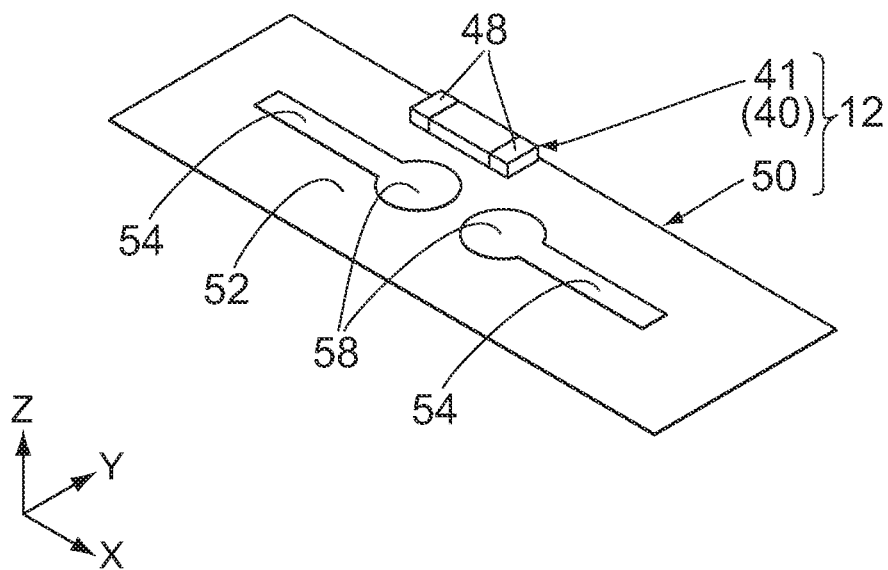
FIG. 19 is a perspective view showing examples of the first circuit member and the second circuit member of the device material set of FIG. 7.

FIG. 19 shows Example 1. The first circuit member 40 of Example 1 is a single electronic component 41. The electronic component 41 has two of the first contact points 48. The second circuit member 50 of Example 1 has two of the second contact points 58 which correspond to the first contact points 48 of the electronic component 41, respectively. In the device 10 (see FIG. 3), the first contact points 48 are in contact with the second contact points 58, respectively.

Figure 20:
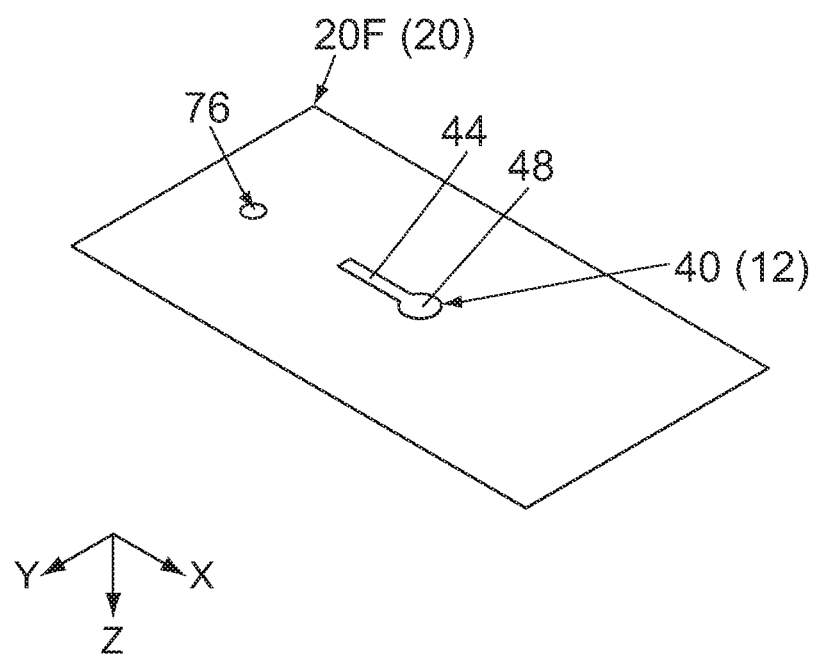
FIG. 20 is a perspective view showing examples of the first film and the first circuit member of the device material set of FIG. 7.

FIG. 20 shows Example 2. The first circuit member 40 of Example 2 is a single first conductive pattern 44 and has the first contact point 48. The first conductive pattern 44 of Example 2 is adhered to or formed on the lower surface of the first film 20F. Thus, the first contact point 48 of Example 2 is proved on the lower surface of the first film 20F.

Figure 21:
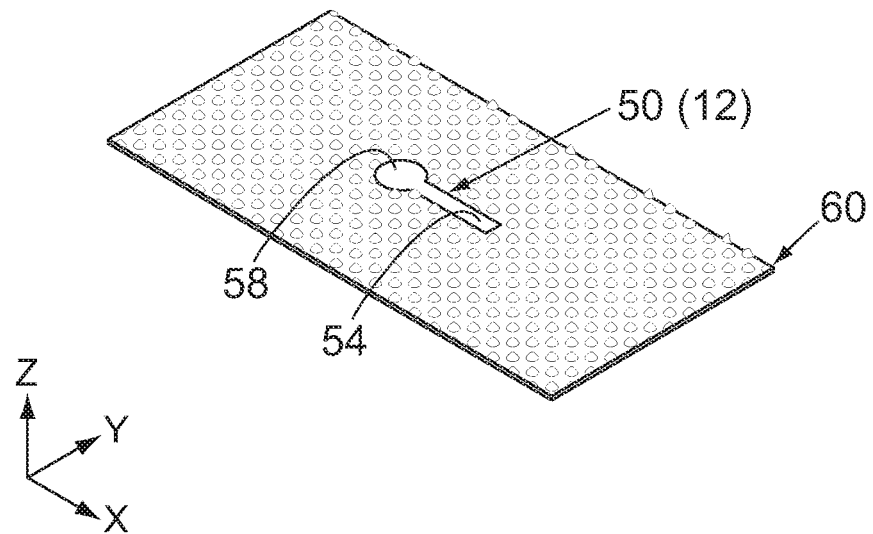
FIG. 21 is a perspective view showing examples of the additional film and the second circuit member of the device material set of FIG. 7.

FIG. 21 shows Example 3. The second circuit member 50 of Example 3 is a single second conductive pattern 54 and has the second contact point 58. The second conductive pattern 54 of Example 3 is adhered to or formed on the upper surface of the additional film 60. Thus, the second contact point 58 of Example 3 is proved on the upper surface of the additional film 60.

Figure 22:
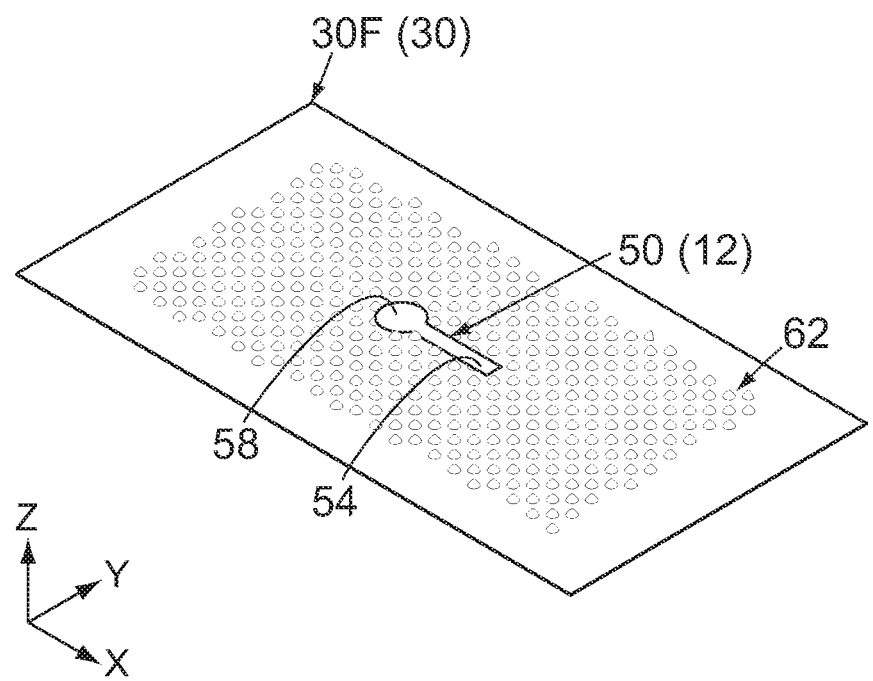
FIG. 22 is a perspective view showing examples of the second film, the additional film and the second circuit member of the device material set of FIG. 7.
Figure 23:
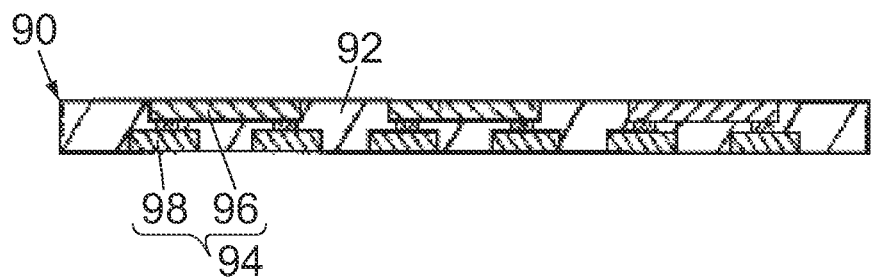
FIG. 23 is a cross-sectional view showing a device of Patent Document 1.

FIG. 22 shows Example 4. The second circuit member 50 of Example 4 is a single second conductive pattern 54 similar to that of Example 3 and has the second contact point 58. The second film 30F of Example 4 is formed with the uneven portion 62. The second conductive pattern 54 of Example 4 is adhered to or formed on the upper surface of the uneven portion 62. Thus, the second contact point 58 of Example 4 is proved on the upper surface of the second film 30F.

While there has been described what is believed to be the preferred embodiment of the invention, those skilled in the art will recognize that other and further modifications may be made thereto without departing from the spirit of the invention, and it is intended to claim all such embodiments that fall within the true scope of the invention.

What is claimed is:

1. A device comprising a first sealing member, a second sealing member, a first circuit member, and a second circuit member, wherein:
    the first sealing member comprises a first film;
    the device defines a closed space;
    the closed space is enclosed by the first sealing member and the second sealing member and is shut off from an outer space outside the device;
    the first circuit member and the second circuit member are shut in the closed space;
    the first circuit member comprises a first contact point;
    the second circuit member comprises a second contact point;
    the first contact point and the second contact point are held pressed against each other by an air pressure difference between an inside and an outside of the closed space, such that the first contact point and the second contact point contact with each other without using a fixing member;
    at least one of the first sealing member and the second sealing member includes an uneven portion, the uneven portion comprising a plurality of projections; and
    the uneven portion is in contact with at least one of the first circuit member and the second circuit member and covers a predetermined region which corresponds to at least one of the first contact point and the second contact point.

2. The device as recited in claim 1, wherein:
    at least one of the first sealing member and the second sealing member comprises an additional film; and
    the additional film has the uneven portion.

3. The device as recited in claim 1, wherein:
    the first film is provided with an air valve; and
    the uneven portion continuously covers a region which extends from the air valve to the predetermined region.

4. The device as recited in claim 3, wherein:
    the first sealing member has a first inner portion and a first outer portion;
    the first inner portion is located inward of the first outer portion;
    the second sealing member has a second inner portion and a second outer portion;
    the second inner portion is located inward of the second outer portion;
    the closed space is enclosed by the first inner portion and the second inner portion;
    the first outer portion has a first seal portion;
    the second outer portion has a second seal portion;
    the first seal portion and the second seal portion are bonded together to form a seal trace; and
    the uneven portion is shut in the closed space.

5. The device as recited in claim 4, wherein the first seal portion and the second seal portion are bonded together by heat-sealing.

6. The device as recited in claim 5, wherein each of the first sealing member and the second sealing member includes two layers consisting of a meltable layer which is meltable by the heat-sealing and an unmeltable layer which is not meltable by the heat-sealing.

7. The device as recited in claim 1, wherein:
    the first sealing member has a first inner portion and a first outer portion;

the first inner portion is located inward of the first outer portion;
the second sealing member has a second inner portion and a second outer portion;
the second inner portion is located inward of the second outer portion;
the closed space is enclosed by the first inner portion and the second inner portion;
the first outer portion has a first seal portion;
the second outer portion has a second seal portion;
the first seal portion and the second seal portion are bonded together to form a seal trace; and
the uneven portion continuously covers a region which extends from the seal trace to the predetermined region.

8. The device as recited in claim 1, wherein the uneven portion entirely covers a region which corresponds to the closed space.

9. The device as recited in claim 1, wherein the second sealing member comprises a second film.

10. The device as recited in claim 9, wherein:
the first film and the second film are two sheet pieces of a single film member which overlap with each other;
the single film member has a predetermined portion; and
the first film and the second film are connected to each other at the predetermined portion.

11. The device as recited in claim 10, wherein:
the single film member is a single planar sheet; and
the first film and the second film are the two sheet pieces which are folded at the predetermined portion to overlap with each other.

12. The device as recited in claim 10, wherein:
the single film member is a single folder-like sheet; and
the first film and the second film are the two sheet pieces which are connected to each other at the predetermined portion.

13. The device as recited in claim 1, wherein:
the first circuit member is a member distinct and separable from the first sealing member; and
the second circuit member is a member distinct and separable from the second sealing member.

14. The device as recited in claim 1, wherein the first circuit member is a member integral with the first sealing member.

15. The device as recited in claim 1, wherein the second circuit member is a member integral with the second sealing member.

16. The device as recited in claim 1, wherein:
the first circuit member has a first base portion and a first conductive pattern;
the first base portion is formed of an insulation film;
the first conductive pattern is formed on the first base portion and has the first contact point;
the second circuit member has a second base portion and a second conductive pattern;
the second base portion is formed of an insulation film; and
the second conductive pattern is formed on the second base portion and has the second contact point.

17. The device as recited in claim 1 wherein each of the first sealing member and the second sealing member has a barrier property.

18. The device as recited in claim 17 wherein each of the first sealing member and the second sealing member has a barrier property against oxygen.

19. The device as recited in claim 17 wherein each of the first sealing member and the second sealing member has a barrier property against water vapor.

20. A method of forming a device comprising a first sealing member, a second sealing member, a first circuit member, and a second circuit member, the method comprising:
preparing the first sealing member, the second sealing member, the first circuit member, and the second circuit member, the first sealing member comprising a first film, the first film being provided with an air valve, at least one of the first sealing member and the second sealing member being provided with an uneven portion comprising a plurality of projections, the first circuit member comprising a first contact point, and the second circuit member comprising a second contact point;
stacking the first sealing member, the first circuit member, the second circuit member, and the second sealing member on each other in this order, with the first contact point and the second contact point facing each other, the uneven portion facing at least one of the first circuit member and the second circuit member, and the uneven portion covering a predetermined region which corresponds to at least one of the first contact point and the second contact point;
shutting the first circuit member and the second circuit member in an inner space which is defined in the device, the inner space being enclosed by the first sealing member and the second sealing member and being shut off from an outer space outside the device except for the air valve; and
vacuuming the inner space by using the air valve so that the first contact point and the second contact point are brought into contact with each other.

* * * * *